US012558237B2

(12) United States Patent
Goldfarb et al.

(10) Patent No.:     US 12,558,237 B2
(45) Date of Patent:     \*Feb. 24, 2026

(54) SYSTEM AND METHOD FOR PROVIDING BIOMECHANICALLY SUITABLE RUNNING GAIT IN POWERED LOWER LIMB DEVICES

(71) Applicant: Vanderbilt University, Nashville, TN (US)

(72) Inventors: Michael Goldfarb, Franklin, TN (US); Amanda Shultz, Old Hickory, TN (US); Brian Lawson, Nashville, TN (US)

(73) Assignee: Vanderbilt University, Nashville, TN (US)

( \* ) Notice: Subject to any disclaimer, the term of this patent is extended or adjusted under 35 U.S.C. 154(b) by 956 days.

This patent is subject to a terminal disclaimer.

(21) Appl. No.: 17/731,563

(22) Filed: Apr. 28, 2022

(65) Prior Publication Data

US 2022/0331130 A1     Oct. 20, 2022

Related U.S. Application Data

(62) Division of application No. 16/383,052, filed on Apr. 12, 2019, now Pat. No. 11,318,028, which is a
(Continued)

(51) Int. Cl.
*A61F 2/68*          (2006.01)
*A61F 2/60*          (2006.01)
(Continued)

(52) U.S. Cl.
CPC .................. *A61F 2/70* (2013.01); *A61F 2/60* (2013.01); *A61F 2/68* (2013.01);
(Continued)

(58) Field of Classification Search
CPC ...... A61F 2/64; A61F 2/68; A61F 2/70; A61F 2002/7625; A61F 2002/7635; A61F 2002/704; A61F 2002/701
See application file for complete search history.

(56) References Cited

U.S. PATENT DOCUMENTS

| | | | |
|---|---|---|---|
| 4,685,925 A | 8/1987 | Childress | |
| 4,883,493 A | 11/1989 | Martel | |
(Continued)

FOREIGN PATENT DOCUMENTS

CA          2762265 A1 \* 10/2001   .............. F16F 9/535

OTHER PUBLICATIONS

Alexander, "Exploring Biomechanics: Animals in Motion," Scientific American Library, New York, pp. 18-27 (1992).
(Continued)

*Primary Examiner* — Christie Bahena
(74) *Attorney, Agent, or Firm* — NIXON PEABODY LLP

(57)          ABSTRACT

Systems and methods for a running controller for a lower limb device including at least a powered knee joint are provided. The method includes collecting real-time sensor information for the lower limb device and configuring the lower limb device to a first state in a finite state model for an activity mode including the running mode. The method further includes, based on the sensor information, transitioning the lower limb device from a current state to a subsequent state in the finite state model for the detected mode when a pre-defined criteria for transitioning to the subsequent state is met, and repeating the transitioning until the activity mode changes. In the system and method, the finite state model includes at least one stance state and at least one swing state, where the at least one stance state includes at least one absorption state and at least one propulsion state.

10 Claims, 28 Drawing Sheets

Related U.S. Application Data division of application No. 13/804,263, filed on Mar. 14, 2013, now Pat. No. 10,646,358.

(60) Provisional application No. 61/610,864, filed on Mar. 14, 2012.

(51) Int. Cl.

| | | |
|---|---|---|
| *A61F 2/64* | (2006.01) | |
| *A61F 2/66* | (2006.01) | |
| *A61F 2/70* | (2006.01) | |
| *A61F 2/50* | (2006.01) | |
| *A61F 2/76* | (2006.01) | |

(52) U.S. Cl.

CPC . *A61F 2002/5003* (2013.01); *A61F 2002/607* (2013.01); *A61F 2/64* (2013.01); *A61F 2/6607* (2013.01); *A61F 2002/701* (2013.01); *A61F 2002/704* (2013.01); *A61F 2002/7625* (2013.01); *A61F 2002/7635* (2013.01); *A61F 2002/764* (2013.01)

(56) References Cited

U.S. PATENT DOCUMENTS

| | | | |
|---|---|---|---|
| 5,893,891 | A | 4/1999 | Zahedi |
| 7,799,091 | B2 | 9/2010 | Herr |
| 8,736,087 | B2 | 5/2014 | Mullins |

| | | | |
|---|---|---|---|
| 2004/0064195 | A1 | 4/2004 | Herr |
| 2005/0113973 | A1 | 5/2005 | Endo |
| 2007/0123997 | A1 | 5/2007 | Herr |
| 2009/0265018 | A1 | 10/2009 | Goldfarb |
| 2011/0112447 | A1 | 5/2011 | Hsiao-Wecksler |
| 2011/0213599 | A1 | 9/2011 | Jacobsen |
| 2011/0224803 | A1 | 9/2011 | Goldfarb |
| 2012/0259431 | A1 | 10/2012 | Han |

OTHER PUBLICATIONS

Mensch, G. et al., "Running Patterns of Transfemoral Aputees: A Clinical Analysis," Prosthetics and Orthotics International, vol. 10, pp. 129-134 (1986).

DiAngelo et al., Performance Assessment of the Terry Fox Jogging Prosthesis for Above-Knee Amputees,: Journal of Biomechanics, 22(6): 543-558 (1989).

Zen Chiropractic, "Gait Analysis: You can run, but you can not hide!" published online May 9, 2016.

Novacheck, T. F., "The biomechanics of running," Gait and Posture, vol. 7, pp. 77-95 (1998).

Shorter, K. A., "A portable powered ankle-foot orthosis for rehabilitation," Journal of Rehabilitation Research and Development, 48(4): 459-472 (2011).

McCluney, C. N., "Walter Reed Patients Test Next-Generation Prosthesis," DOD News, published online Dec. 10, 2009.

International Search Report and Written Opinion in International Application No. PCT/US2013/031286, mailed Jun. 28, 2013.

* cited by examiner

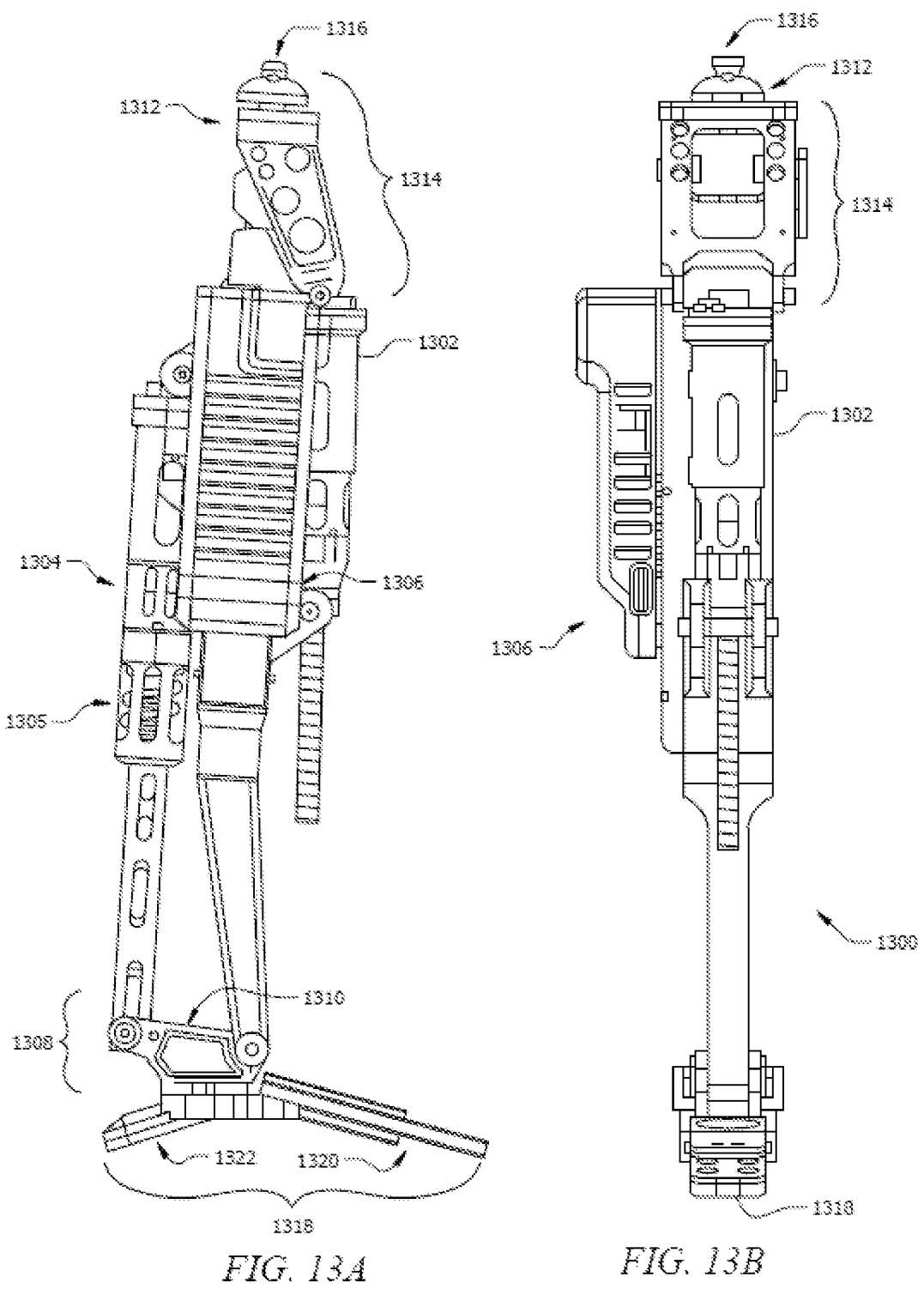
*FIG. 13A*          *FIG. 13B*

SYSTEM AND METHOD FOR PROVIDING BIOMECHANICALLY SUITABLE RUNNING GAIT IN POWERED LOWER LIMB DEVICES

CROSS-REFERENCE TO RELATED APPLICATIONS

This application is a division of U.S. patent application Ser. No. 16/383,052, filed on Apr. 12, 2019, which is now allowed; U.S. patent application Ser. No. 16/383,052 is a division of U.S. patent application Ser. No. 13/804,263, filed Mar. 14, 2013, which issued as U.S. Pat. No. 10,646,358 on May 12, 2020, which claims priority to and the benefit of U.S. Provisional Application No. 61/610,864, filed Mar. 14, 2012 and entitled "CONTROL METHODOLOGY FOR BIOMECHANICALLY NORMAL RUNNING WITH A POWERED PROSTHESIS", the contents of which are herein incorporated by reference in their entirety.

FIELD OF THE INVENTION

The present invention relates to apparatus and methods for controlling lower limb devices, including prostheses or orthoses, in order to provide a biomechanically suitable running gait in such devices.

BACKGROUND

In 2005, approximately 623,000 cases of lower limb amputation existed in the United States, with the total number of cases of limb loss expected to increase by approximately 40% by the year 2020. Lower-limb prostheses exist in large part to improve the mobility of the user, particularly concerning activities involved in daily living. Dedicated sports prostheses also exist for activities such as running, field events, cycling, swimming, golf, etc., which are used for competition and recreation alike. Many of these devices have been proven quite effective, some having even been accused of providing an unfair advantage to the user. However, should the need arise during the course of normal daily activity for a lower-limb amputee to run—perhaps to quickly dodge an oncoming vehicle or to catch a bus—the individual's daily use prosthesis would be called upon to meet that need.

The majority of prostheses currently available to lower limb amputees are energetically passive. Passive prostheses are unable to reproduce the biomechanics of healthy running in part because these biomechanics require significant net positive power at both the knee and ankle joints. In recent years, powered lower limb prostheses, which are able to produce net positive power at the knee or ankle joints, have started to emerge. However, none of these devices incorporate both a powered knee and ankle (defined as able to produce biomechanically significant net positive power at each joint over a stride). Moreover, none of these devices have demonstrated restoration of healthy gait characteristics for running in transfemoral amputees. Relative to walking, biomechanically healthy running is characterized by a substantially greater degree of stance knee flexion and a correspondingly greater degree of ankle dorsiflexion, also in the stance phase. Further, the stance phase of running constitutes less than 50% of the stride cycle, while the stance phase of walking constitutes greater than 50%. As such, a walking gait is typically characterized by a double support phase, while a running gait is typically characterized by a double float (or flight) phase, i.e., a phase/in which both feet are off the ground. In order to provide the latter, each leg must generate an amount of vertical propulsive energy greater than or equal to the amount absorbed during each stance phase of gait. Since the foot/ground collision will always realistically involve some energy loss, each leg must in fact generate an amount of propulsive energy strictly greater than the amount absorbed. In order to do so, the joints of a running leg capable of sustaining a running gait must be powered (i.e., they must be capable of generating more power than they absorb).

SUMMARY

Embodiments of the invention concern systems and methods for controlling lower limb devices.

In a first embodiment of the invention, a method of operating a lower limb device comprising at least a powered knee joint is provided. The method includes collecting real-time sensor information for the lower limb device and configuring the lower limb device to a first state in a finite state model for an activity mode comprising the running mode. The method also includes, based on the sensor information, transitioning the lower limb device from a current state to a subsequent state in the finite state model for the detected mode when a pre-defined criteria for transitioning to the subsequent state is met. The method further includes repeating the transitioning until the activity mode changes. In the method the finite state model comprises at least one stance state and at least one swing state, and wherein the at least one stance state comprises at least one absorption state and at least one propulsion state.

In the method, the transitioning can include causing the powered knee joint to dissipate an first amount of power during the at least one absorption state, and causing the powered knee joint to generate a second amount of power during at least one propulsion state, where the second amount of power is at least equal to the first amount of power. The transitioning can further include, when the at least one powered joint further comprises a powered ankle joint, causing the powered knee joint and the powered ankle joint to simultaneously dissipate power substantially throughout the at least one absorption state, and causing the powered knee joint and the powered ankle joint to simultaneously generate power substantially throughout the at least one propulsion state.

In the method, the transitioning can also include causing the at least one powered joint to emulate a passive impedance during the at least one absorption state. The passive impedance can be at least one of a stiffness component or a damping component.

In the method, the pre-defined criteria associated with a transition between the at least one absorption state and the at least one propulsion state can be associated with at least one of a motion in at least one powered joint of the lower limb device, a joint angular velocity for at least one powered joint of the lower limb device, and load on the lower limb device.

The method can further include, prior to the configuring, selecting the activity mode for the lower limb device based on the real-time sensor information, where a transition between a walking mode and the running mode is based on a measurement of at least one of a load or acceleration at foot strike, a stance time, a swing time, or a stride time.

In a second embodiment of the invention, there is provided a computer-readable medium having stored thereon a plurality of instructions for causing a controller device for a powered lower limb device to perform any of the methods of the first embodiment.

In a third embodiment of the invention, there is provided a system for controlling a lower limb device comprising at least a powered knee joint. The system includes at least one sensor for collecting real-time sensor information for the lower limb device and at least one processor communicatively coupled to the at least one sensor and to the at least powered knee joint. The system also includes a computer-readable medium, having stored thereon instructions for causing the processor to perform various steps. The steps include generating control signals for at least the powered knee joint to transition the lower limb device to a first state in a finite state model for an activity mode comprising a running mode and generating additional control signals for at least the powered knee joint to transition the lower limb device from a current state to a subsequent state in the finite state model when a pre-defined criteria for transitioning to the subsequent state is met based on the real-time sensor information. The steps also include repeating the generating of the additional control signals transitioning until the activity mode changes. In the system, the finite state model comprises at least one stance state and at least one swing state, and wherein the at least one stance state comprises at least one absorption state and at least one propulsion state.

In the system, the instructions can cause the processor to generate the control signals for the at least one absorption state to cause the powered knee joint to dissipate an first amount of power during the at least one absorption state and to generate the control signals for the at least one propulsion state to cause the powered knee joint to generate a second amount of power during the at least one propulsion state, and where the second amount of power is at least equal to the first amount of power. Further, where the at least one powered joint further comprises a powered ankle joint, the instructions can cause the processor to generate the control signals for the at least one absorption state to cause the powered knee joint and the powered ankle joint to simultaneously dissipate power substantially throughout the at least one absorption state and to generate the control signals for the at least one propulsion state to cause the powered knee joint and the powered ankle joint to simultaneously generate power substantially throughout the at least one propulsion state.

The instructions can also cause the processor to cause the at least one powered joint to emulate a passive impedance during the at least one absorption state. The passive impedance can be at least one of a stiffness component or a damping component.

In the system, the pre-defined criteria associated with a transition between the at least one absorption state and the at least one propulsion state is associated with at least one of a motion in at least one powered joint of the lower limb device, a joint angular velocity for at least one powered joint of the lower limb device, and load on the lower limb device.

Further, the computer-readable medium further comprises instructions for causing the processor to perform the step of, prior to the generating of the control signals, selecting the running mode for the lower limb device based on the real-time sensor information, wherein a transition between a walking mode and the running mode is based on a measurement of at least one of a load or acceleration at foot strike, a stance time, a swing time, or a stride time.

BRIEF DESCRIPTION OF THE DRAWINGS

FIG. 13A is a side view of powered knee and ankle prosthesis, according to another embodiment of the invention;

FIG. 13B is a front view of powered knee and ankle prosthesis of FIG. 13A.

5

Figure 23:
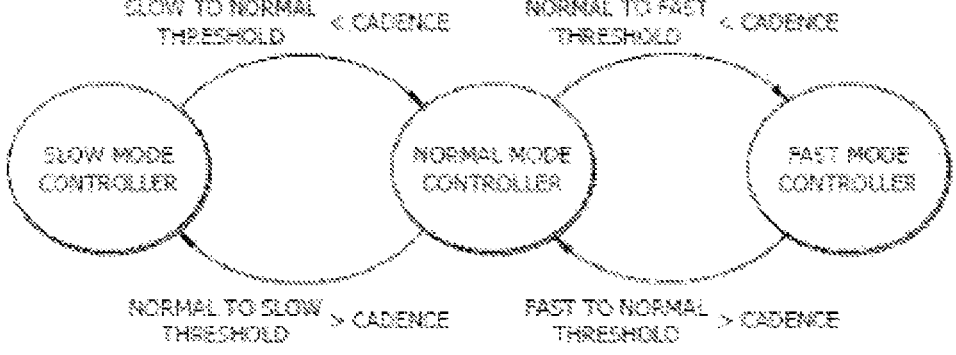
Figure 24:
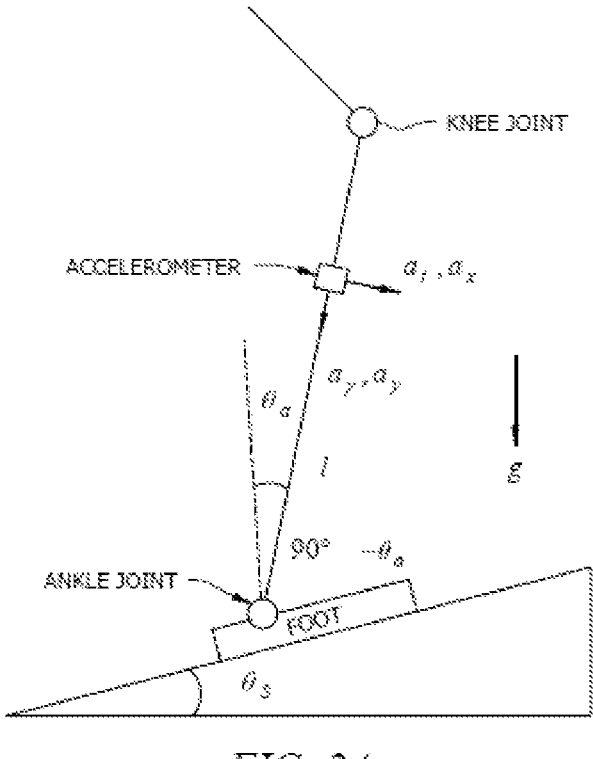
Figure 25:
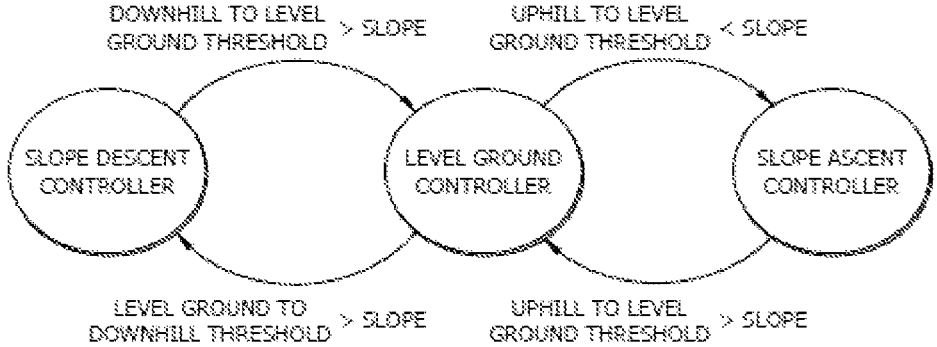
Figures 26A, 26B:
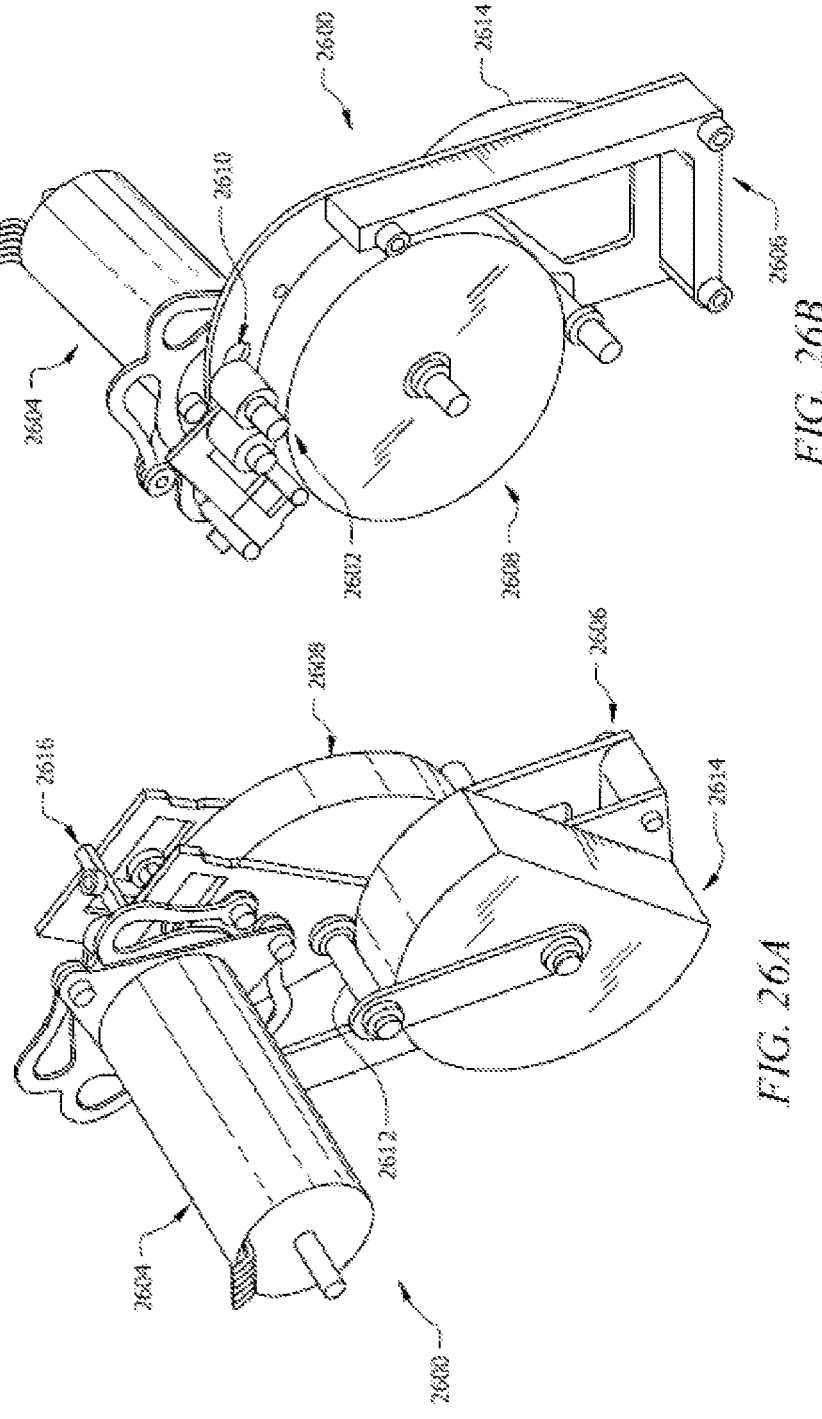
Figure 27:
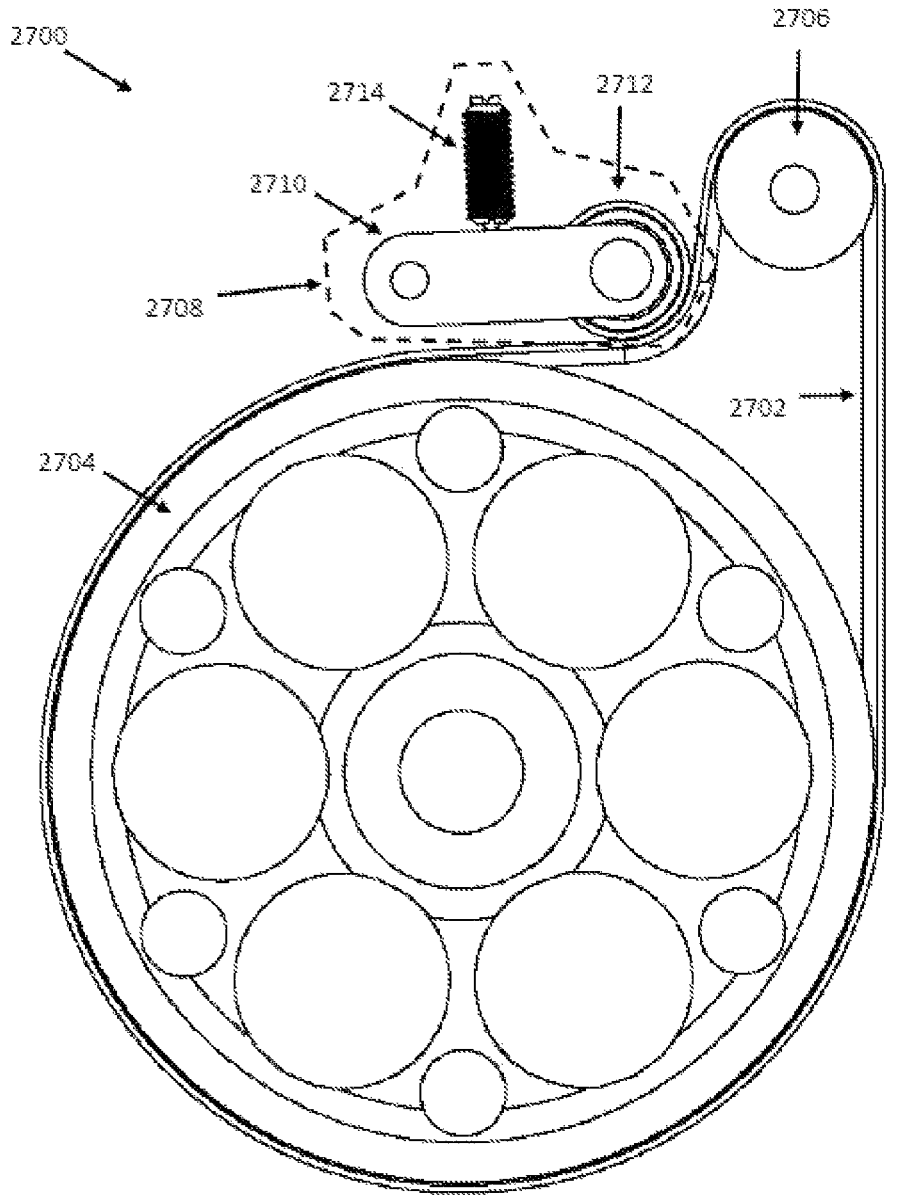
Figure 28:
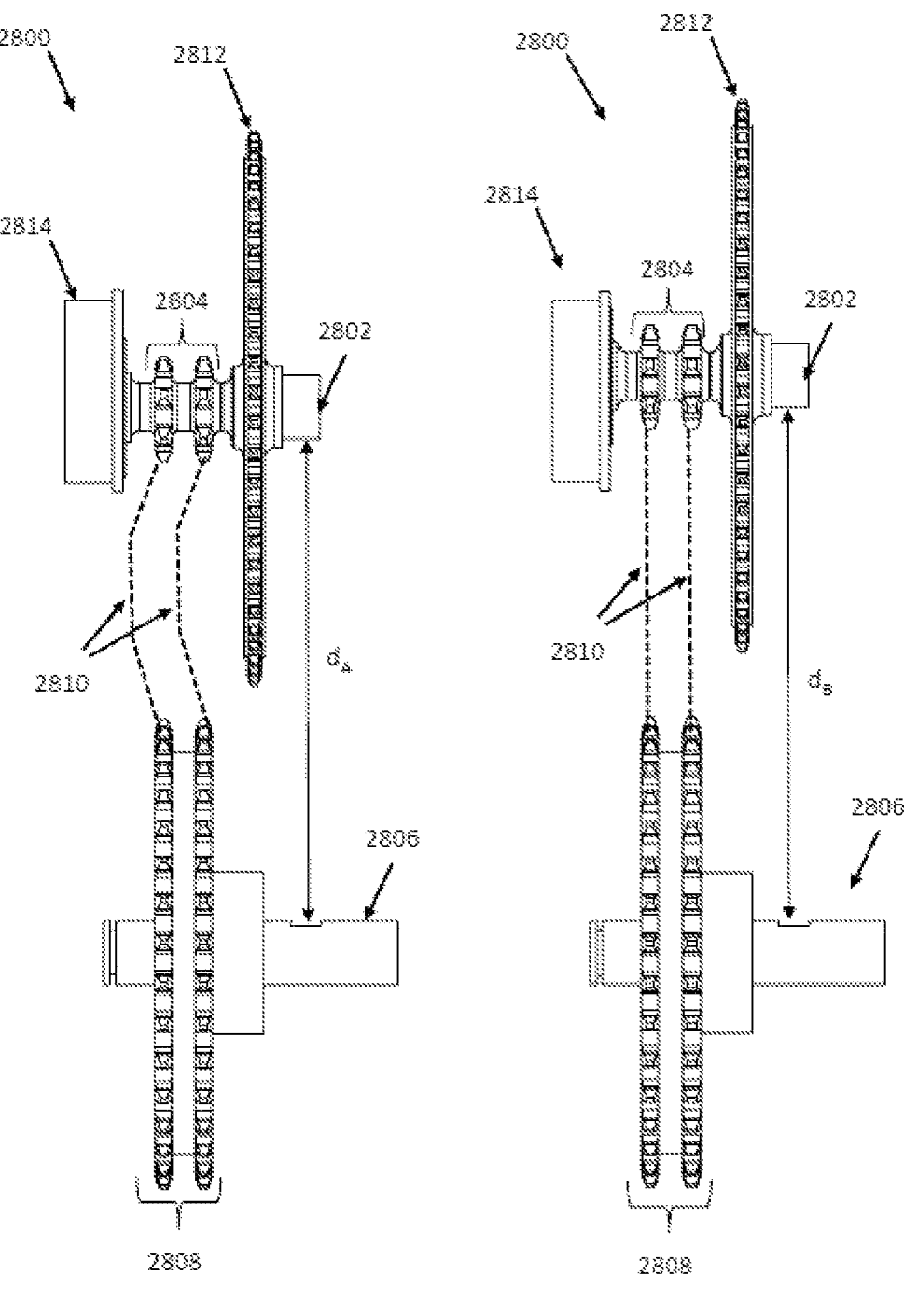
Figure 29:
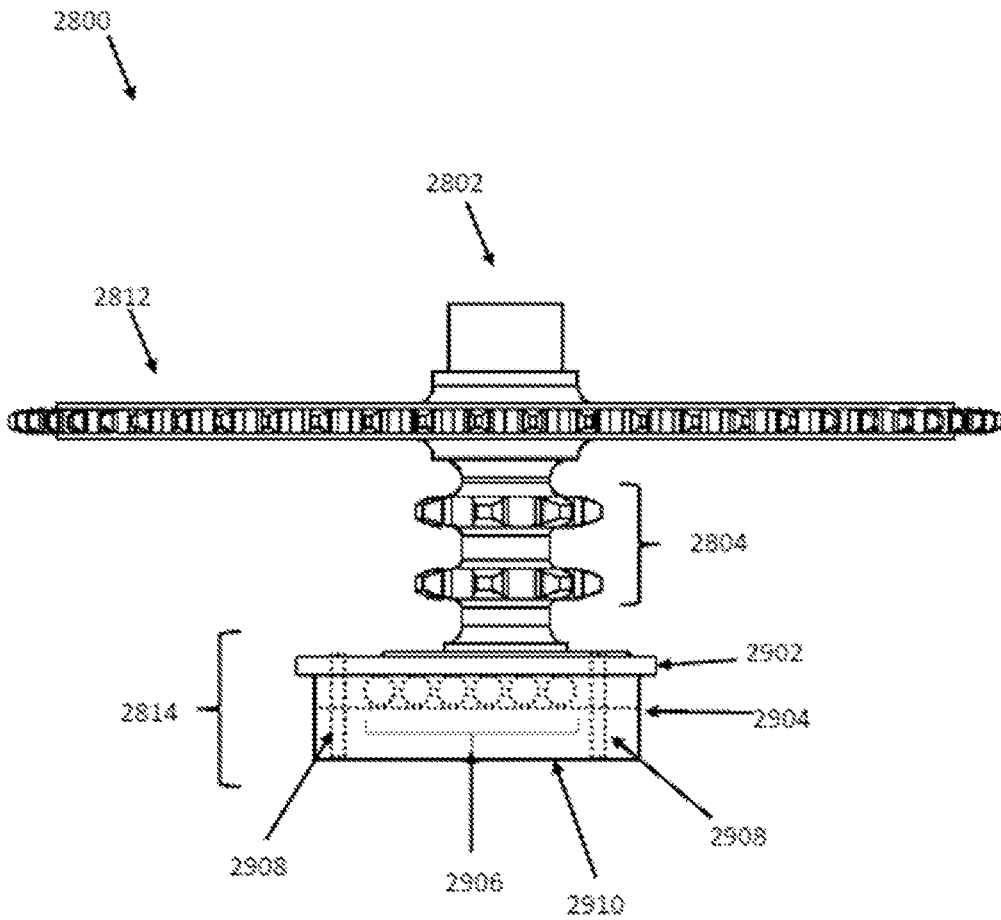
Figure 30:
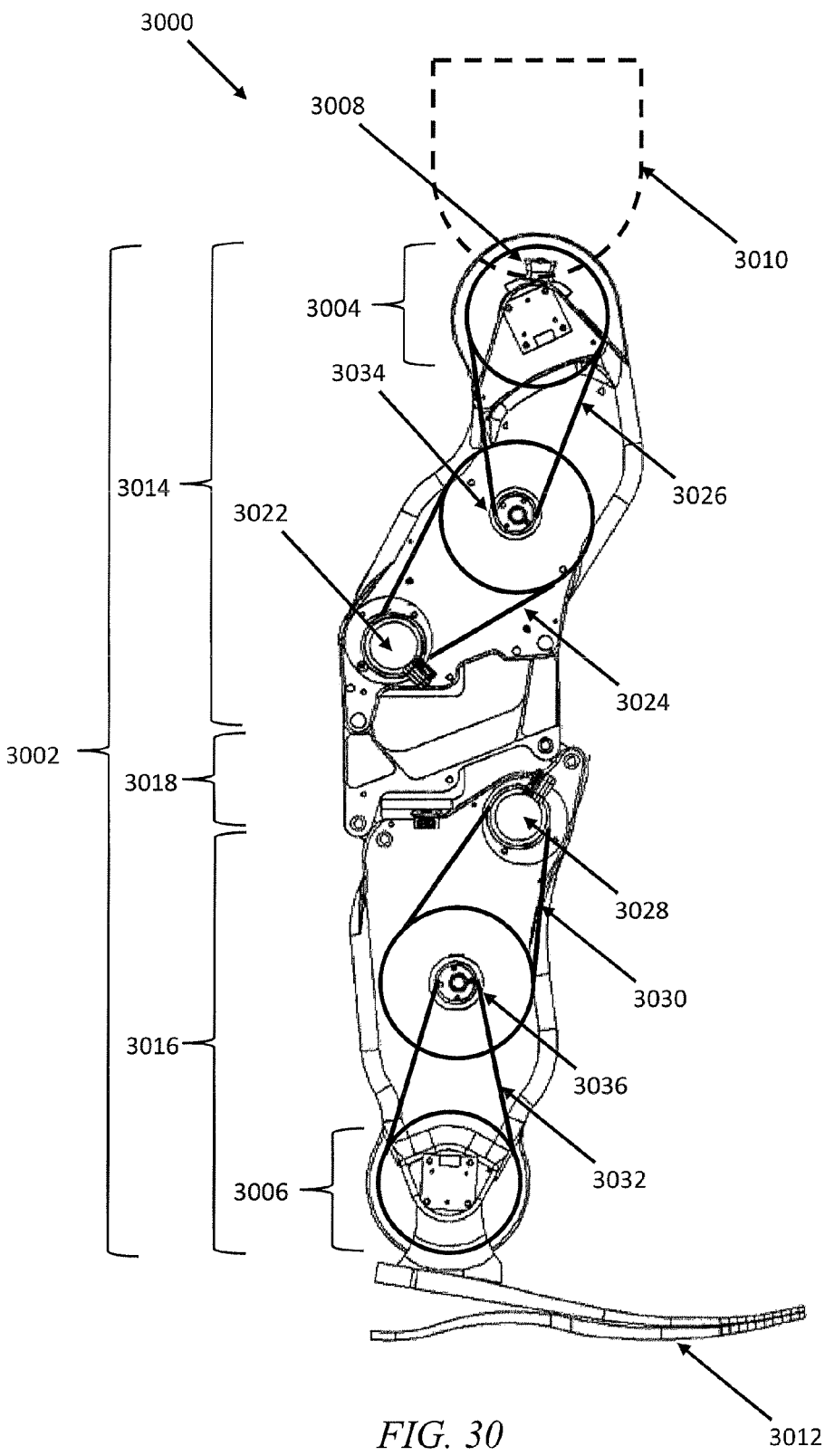
Figure 31:
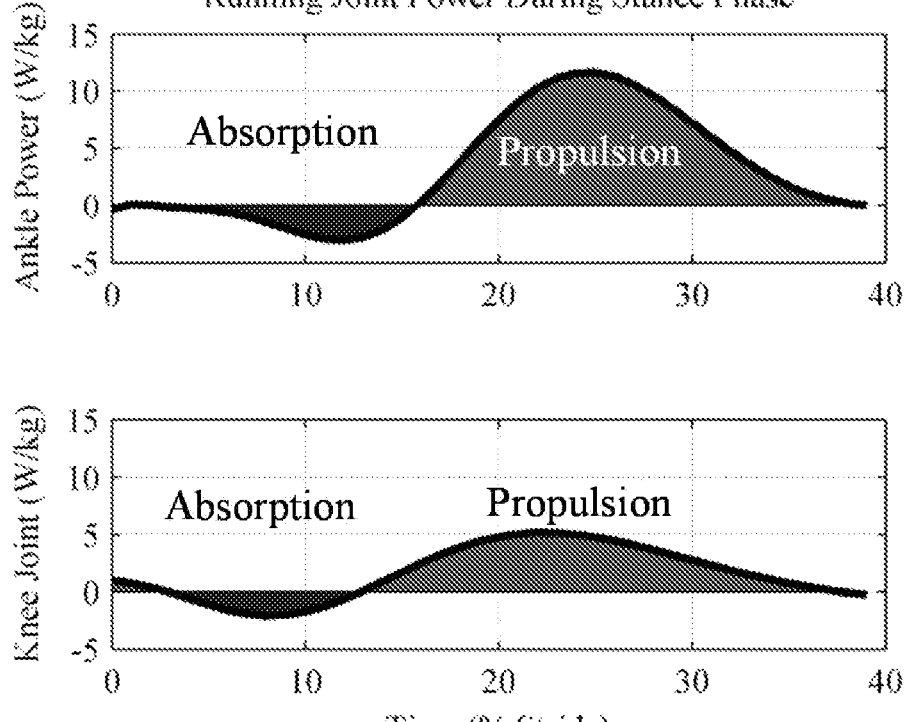
Figure 32:
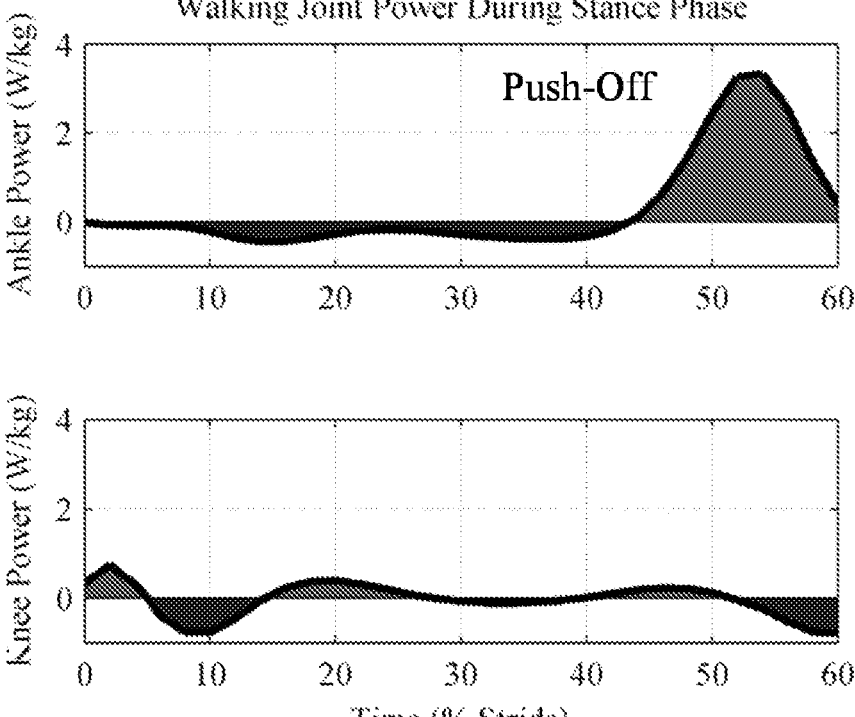
Figure 33:
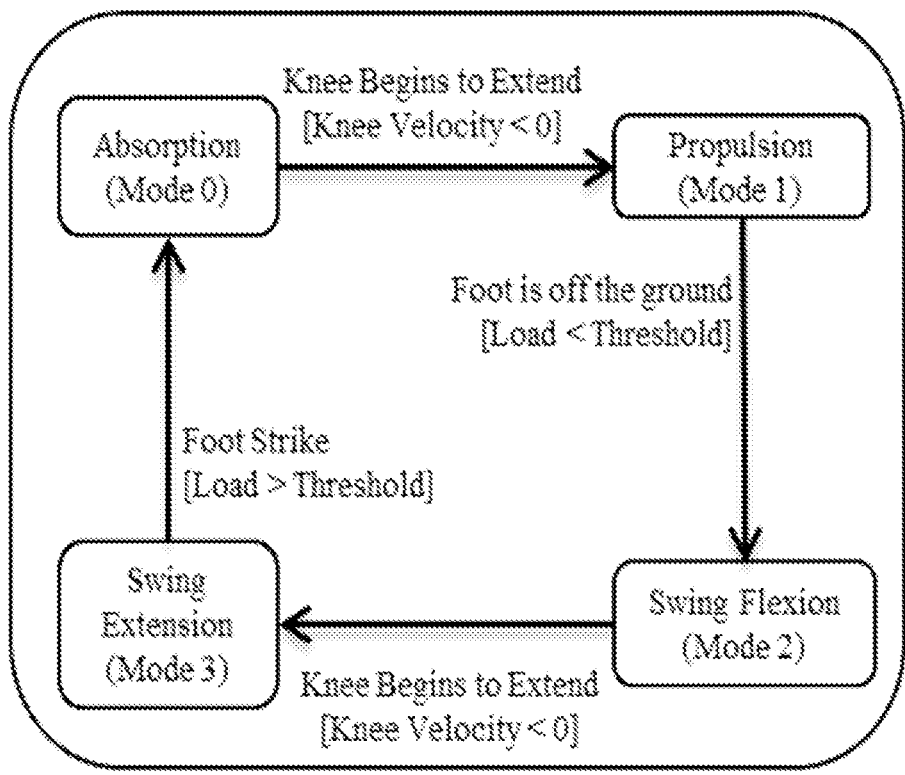
Figure 34:
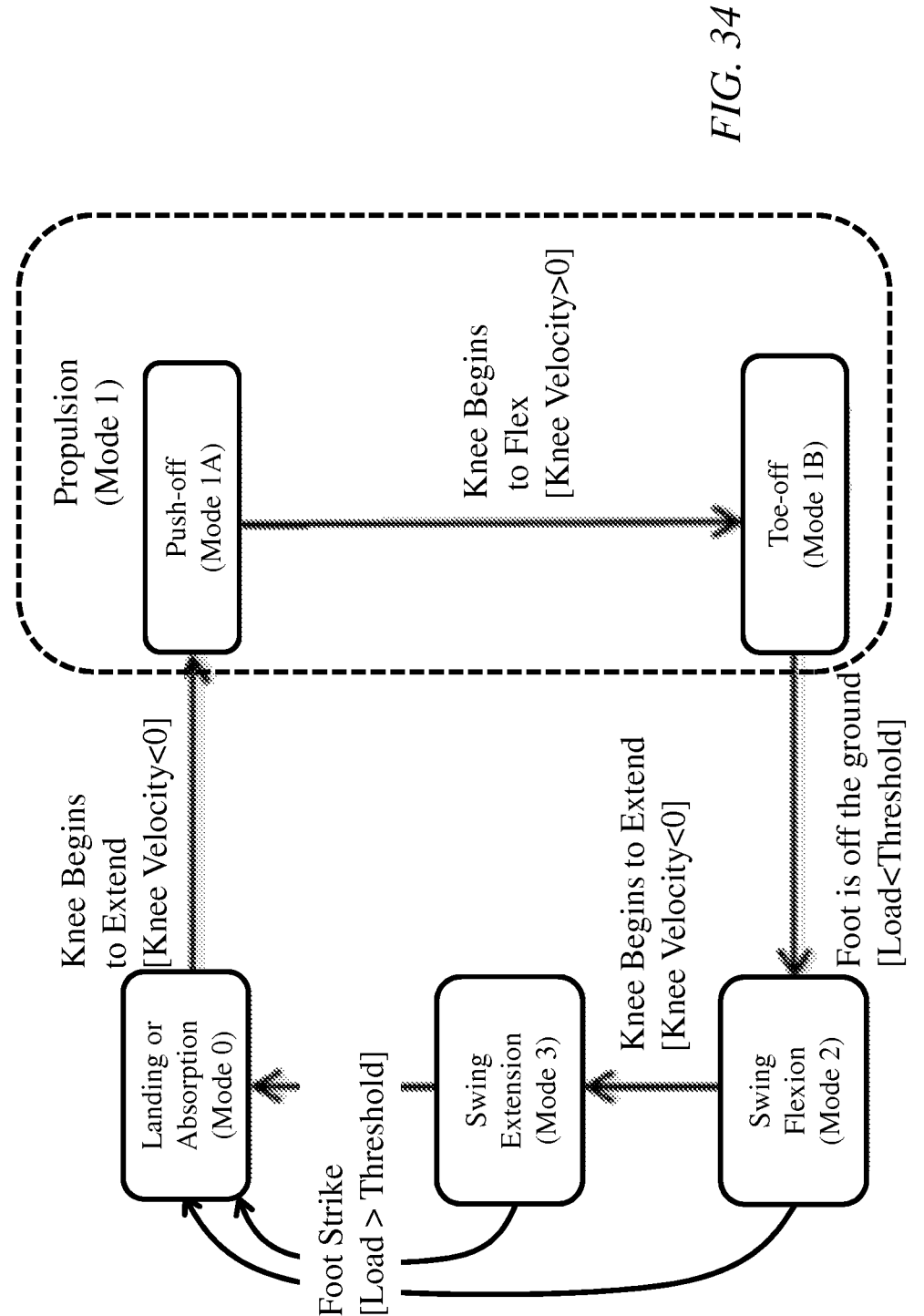
Figures 35, 36:
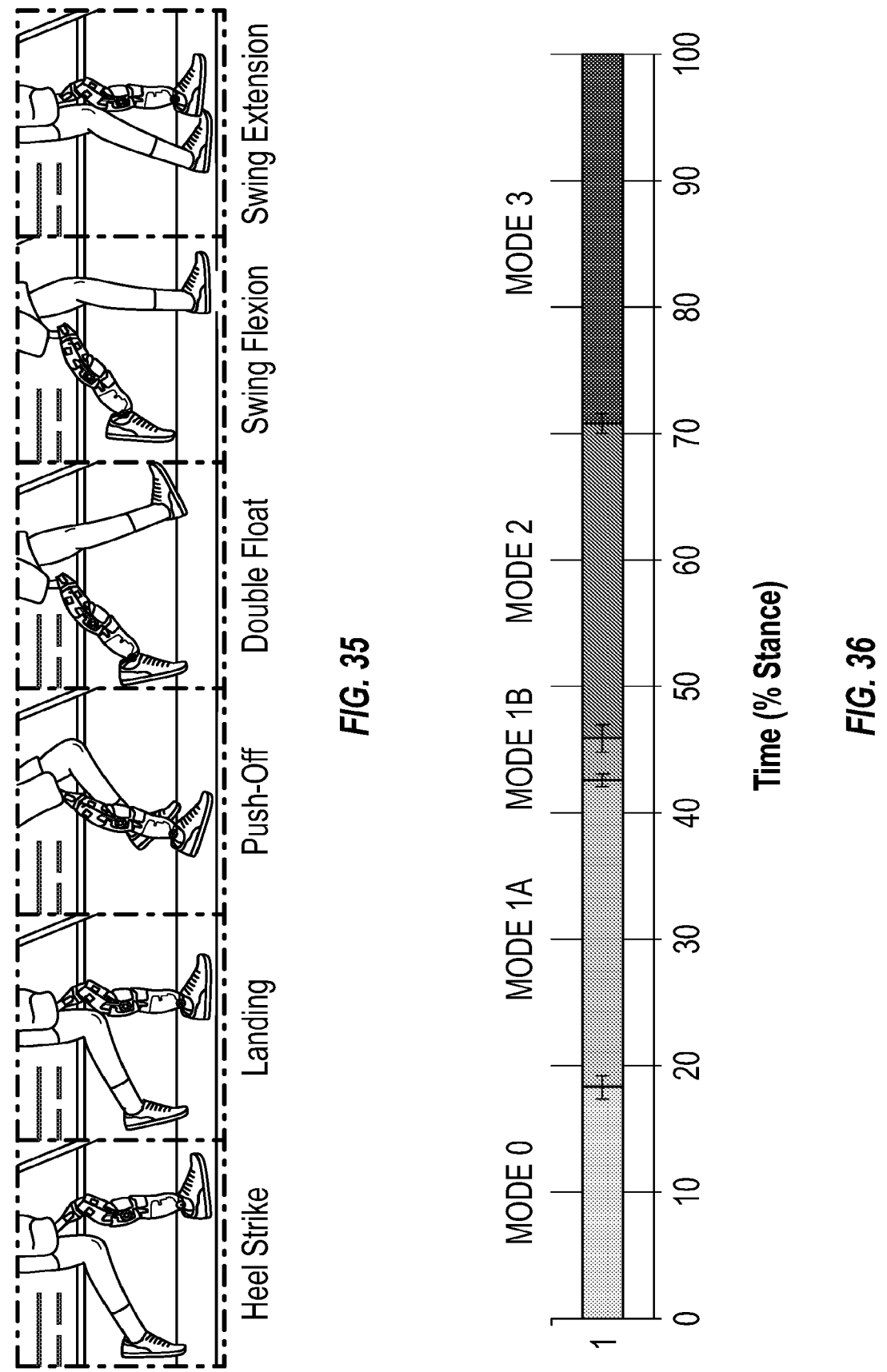
Figure 37:
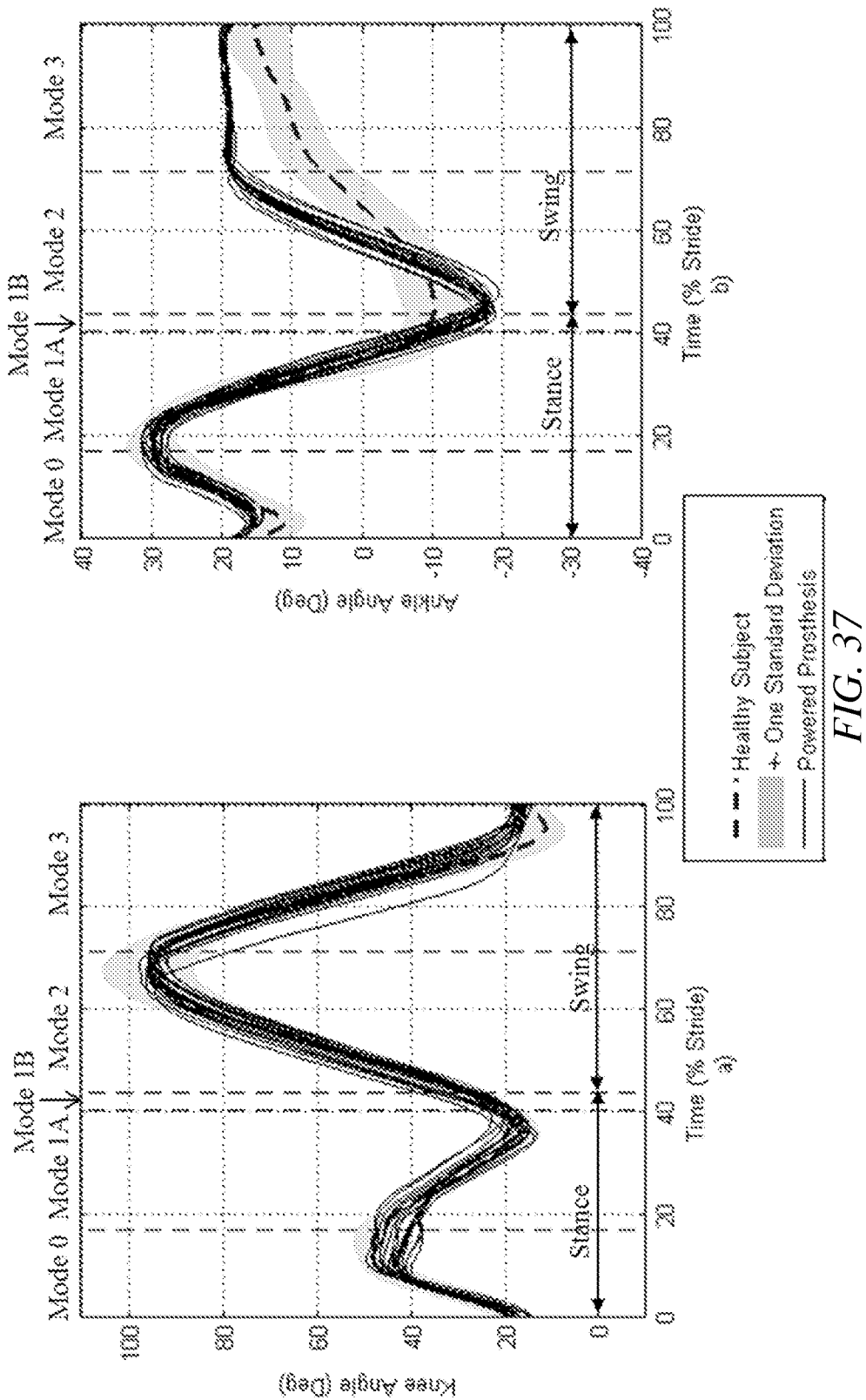

FIG. 23 is a state chart for governing the discrete dynamics of the cadence estimator in accordance with an embodiment of the invention;

FIG. 24 is a schematic diagram of accelerometer measurements for slope estimation in accordance with an embodiment of the invention;

FIG. 25 is a state chart for slope estimation in a controller in accordance with an embodiment of the invention;

FIGS. 26A and 26B show front and back views of a friction/cable drive motor in accordance with an embodiment of the invention;

FIG. 27 shows an exemplary embodiment of a belt drive transmission in accordance with an embodiment of the invention;

FIGS. 28A and 28B show side views of first and second positions, respectively, achievable for an exemplary embodiment of a chain drive transmission including an eccentric mount in accordance with an embodiment of the invention;

FIG. 29 illustrates schematically the components for the adjustable bearing mounts in FIGS. 28A and 28B;

FIG. 30 illustrates an exemplary configuration of a powered leg prosthesis in accordance with the embodiments shown in FIGS. 27-29;

FIG. 31 shows the (body-mass-normalized) power characteristics of the knee and ankle joints during the stance phase of running for healthy subjects;

FIG. 32 shows the (body-mass-normalized) power characteristics of the knee and ankle during the stance phase of walking for healthy subjects;

FIG. 33 shows an exemplary running controller for a powered prosthesis with a knee and ankle joint;

FIG. 34 shows a specific implementation for the exemplary running controller of FIG. 33;

FIG. 35 depicts six key elements of a stride captured from a video taken during one trial;

FIG. 36 depicts the mode transitions (percent of stride) ±one standard deviation as recorded during the running controller evaluations; and FIG. 37 compares thirteen strides of the amputee subject running on the powered prosthesis to the sagittal plane knee and ankle joint angles of healthy subjects.

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

In view of the limitations of existing lower limb prostheses and other lower limb devices, the various embodiments are directed to a new control algorithm (i.e., a running controller) that enables a biomechanically appropriate or suitable running gait for lower limb devices. When such a running controller is implemented in a powered prosthesis comprising at least a powered knee joint and optionally a powered ankle joint, the incorporated running controller can enable amputees with such a prosthesis to have a running gait closely representative of biomechanically healthy running, including the appropriate aforementioned joint kinematics and the double float phase of gait.

Although the various embodiments will be described primarily with respect to the incorporation of the running controller into a control system for a lower limb prosthesis, the various embodiments are not limited in this regard. Rather, the running controller can also be utilized in any type of lower limb devices, including, but not limited to, powered orthotic devices or other lower limb assistive devices. Further, although the various embodiments will be described with respect to a lower limb prosthesis including a powered knee joint and a powered ankle joint (e.g., for transfemoral amputees), the various embodiments are not limited in this regard. Rather, the running controller can also be used to improve running gait for lower limb prostheses for amputees with an intact knee joint (i.e., for transtibial amputees).

Prior to discussing the running, the disclosure first turns to FIGS. 1A-30 where there are described various configurations for powered leg and ankle prostheses, including a controller, which can be modified to include a running controller in accordance with the various embodiments of the invention.

Exemplary Prosthesis Configurations

A first design for a prosthesis for use in the various embodiments of the invention is shown in FIG. 1A through FIG. 6B. The prosthesis 100 comprises a prosthetic lower leg 101. Lower leg 101 can be coupled to a powered knee joint comprising a knee motor unit 105 coupled to a knee joint 110, and a powered ankle joint comprising an ankle motor 115 coupled to an ankle joint 120. A sagittal plane moment sensor 125 can be located between the prosthesis and the user to measure the moment, and in one embodiment is located immediately below the socket interface. In the embodiment shown, sensor 125 measures the sagittal plane moment, while separate sensors described below measure the ball of foot force and heel force with respect to the ground or other object the foot is pressed against. A load sensor 135 can be positioned at the ball of the foot, and a load sensor 140 can be positioned at the heel of the foot. However, in another embodiment (not shown) sensor 125 can measure the sagittal plane moment, the frontal plane moment and the axial force, such as provided by the three-axis socket load cell. This alternate embodiment can eliminate the need for sensor 135 and sensor 140.

Figure 4:
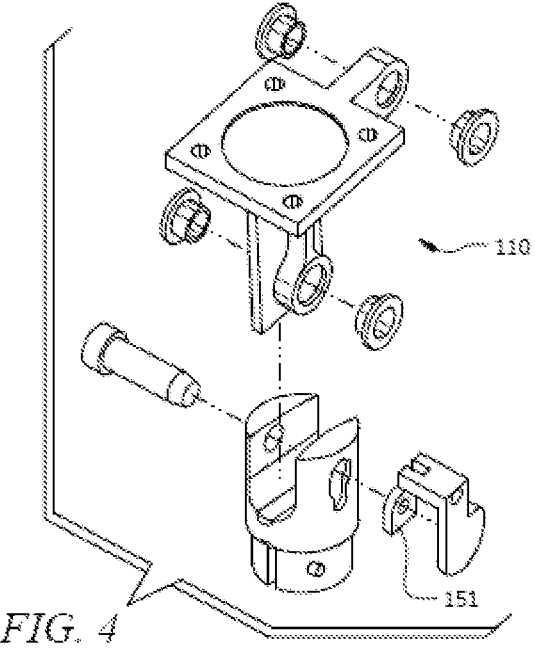
FIG. 4 is an exploded view of knee joint, according to an embodiment of the invention.
Figure 5:
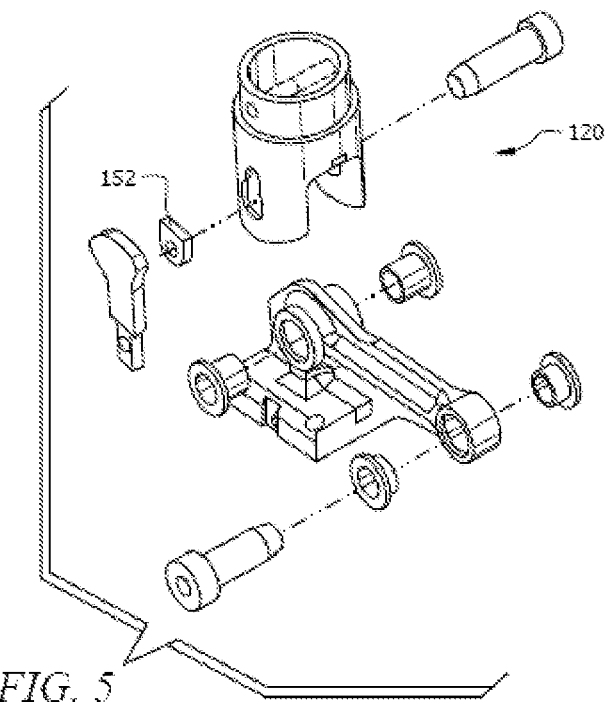
FIG. 5 is an exploded view of ankle joint, according to an embodiment of the invention.

Load sensors 141 and 142 are in series with each motor unit 105 and 115, respectively for motor unit force control. Position sensors 151 and 152 are provided at each joint 110 and 120 as shown in FIGS. 4 and 5 respectively. Position sensors 151 measure joint angle ($\theta$ as used below) and can be embodied as potentiometers. The computer/process controller, and power source (e.g. a battery such as a Li ion battery, and electrical connections in the case of an electrical power source are not shown to avoid obscuring aspects of the invention. Non-electrical power sources may also be used, such as pneumatic power, or non-battery electrical sources, such as hydrogen-based fuel cells.

Figure 1A:
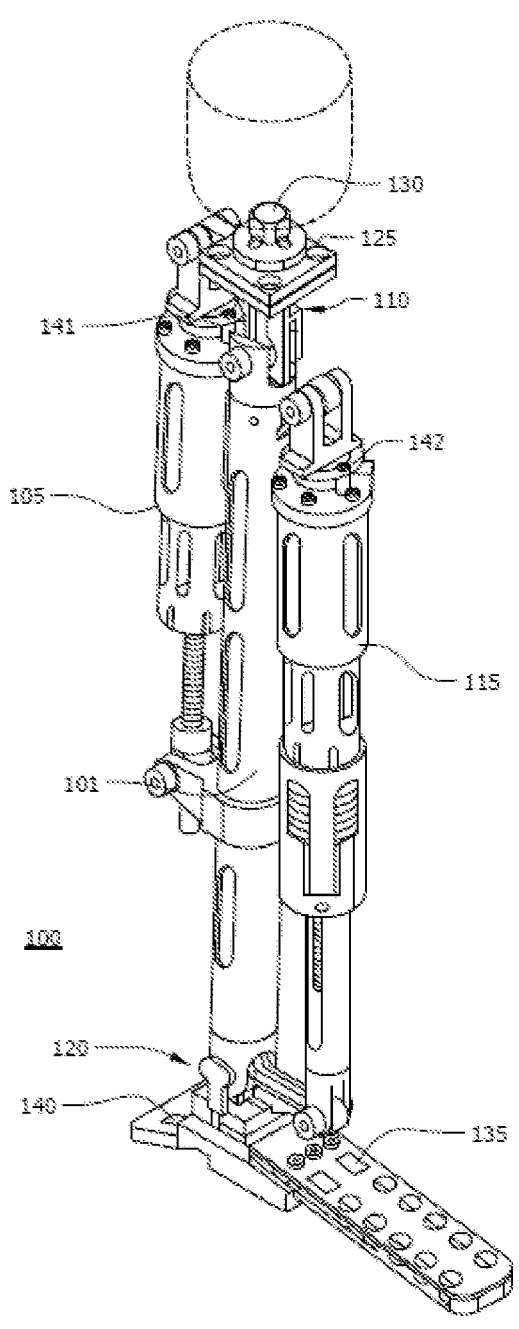
FIG. 1A is a view of a powered knee and ankle prosthesis, according to an embodiment of the invention.
Figure 1B:
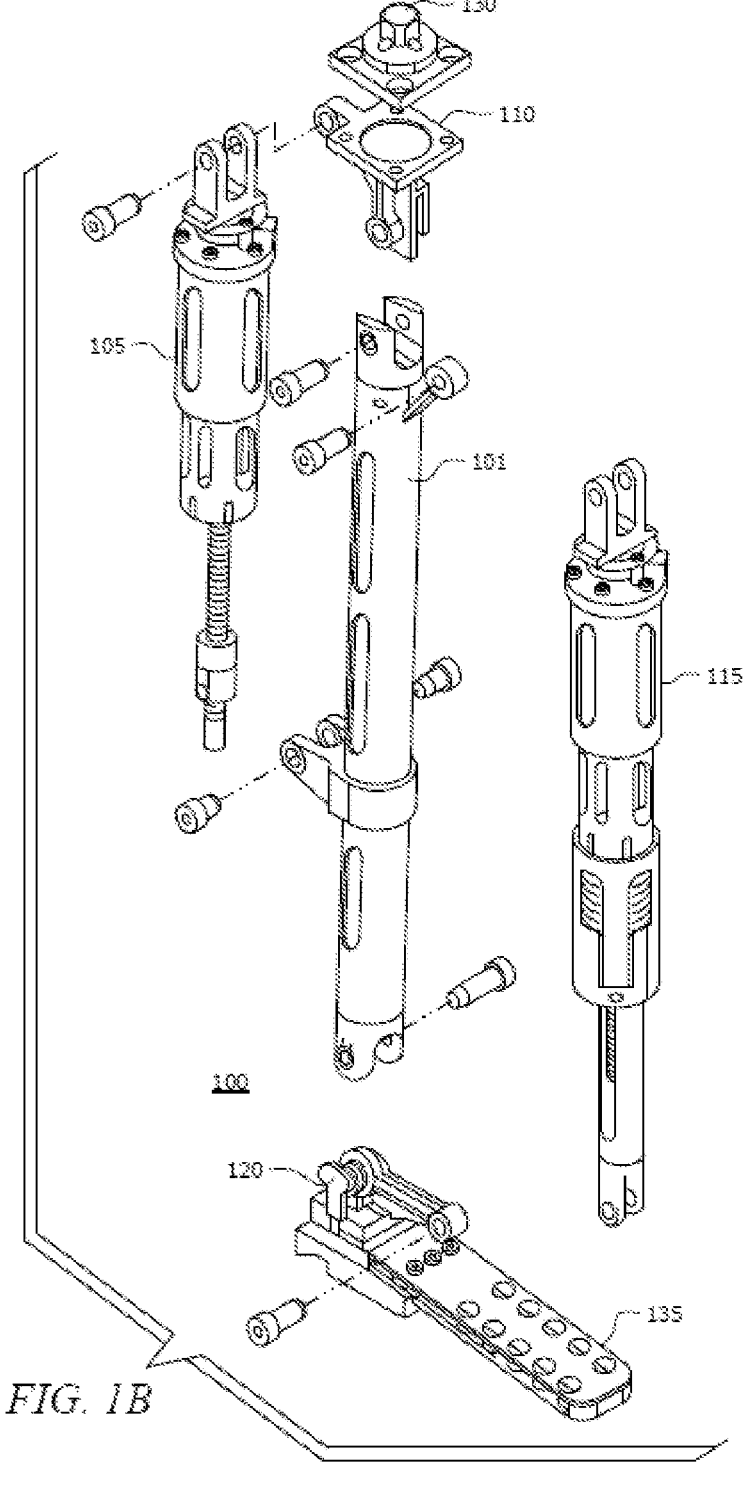
FIG. 1B is an exploded view of the powered knee and ankle prosthesis shown in FIG. 1A, according to an embodiment of the invention.

Prosthesis 100 is shown in an exploded view in FIG. 1B. Joints 110 and 120 are more clearly shown as compared to FIG. 1A.

Figures 2, 3:
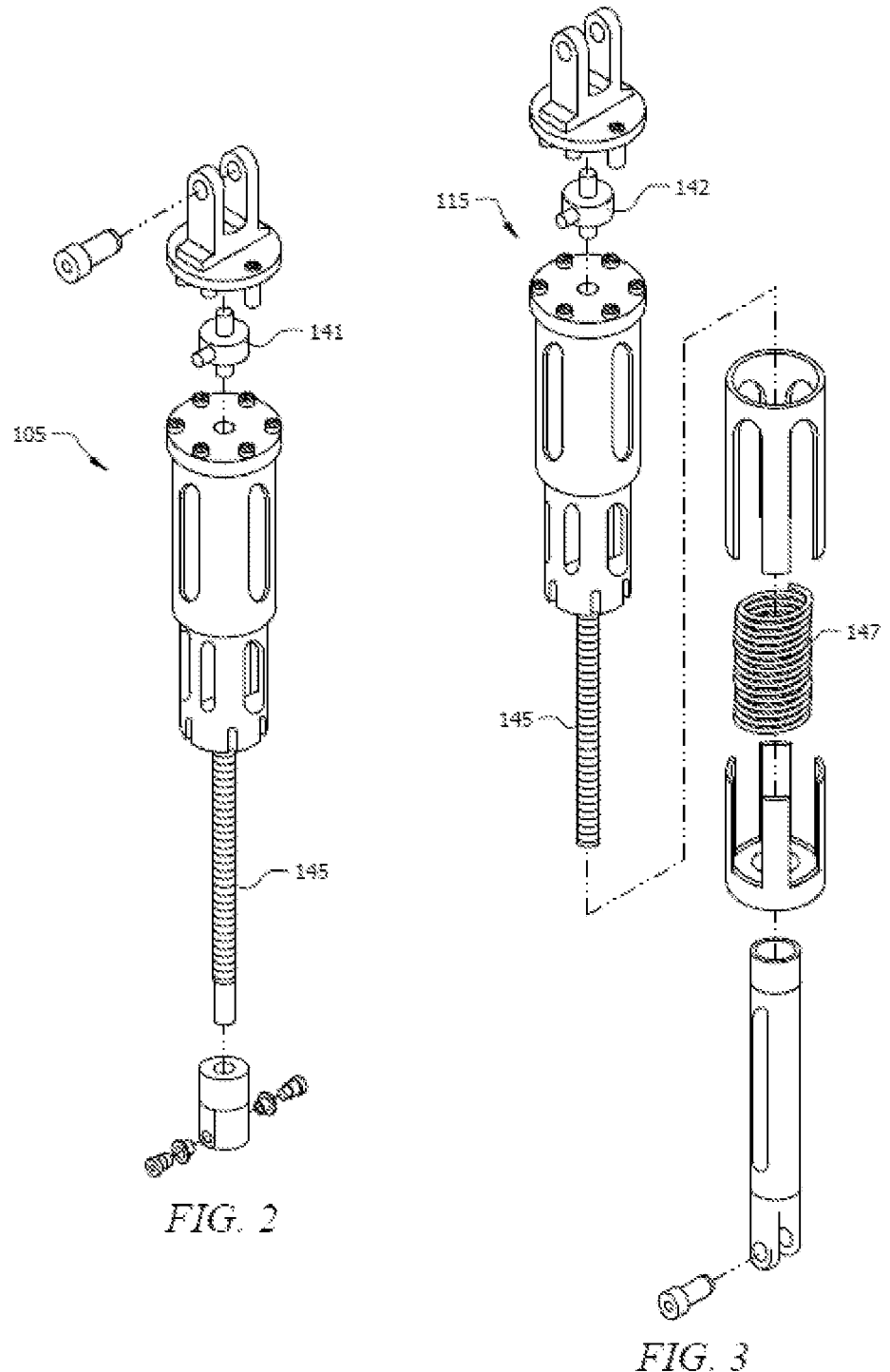
FIG. 2 is an exploded view of knee motor unit, according to an embodiment of the invention.
FIG. 3 is an exploded view of ankle motor unit, according to an embodiment of the invention.

FIG. 2 is an exploded view of knee motor unit 105, according to an embodiment of the invention. Load sensor 141 is shown as a load cell (e.g. strain gauge). Load sensor 141 measures force and moments. The motor unit 105 comprises a motor-driven ball screw assembly which drives the knee joint through a slider-crank linkage comprising screw 145. Other motor drive assemblies may also generally be used.

FIG. 3 is an exploded view of ankle motor unit 115, according to an embodiment of the invention. Load sensor 142 is generally analogous to load sensor 141. The motor unit 115 comprises a motor-driven ball screw assembly which drives the ankle joint through a slider-crank linkage comprising screw 145. The ankle motor 115 includes a spring 147 positioned to provide power in parallel (thus being additive) with power provided by the motor unit 115. Spring 147 biases the motor unit's force output toward ankle plantarflexion, and supplements the power output provided by motor unit 115 during ankle push off.

FIG. 4 is an exploded view of knee joint. 110, according to an embodiment of the invention. As described above, knee joint 110 includes position sensor 151 that can be embodied as a potentiometer for angle measurements of the knee joint 110.

FIG. 5 is an exploded view of ankle joint 120, according to an embodiment of the invention. As described above, ankle joint 120 includes position sensor 152 that can be embodied as a potentiometer for angle measurements of the ankle joint 120.

Figure 6A:
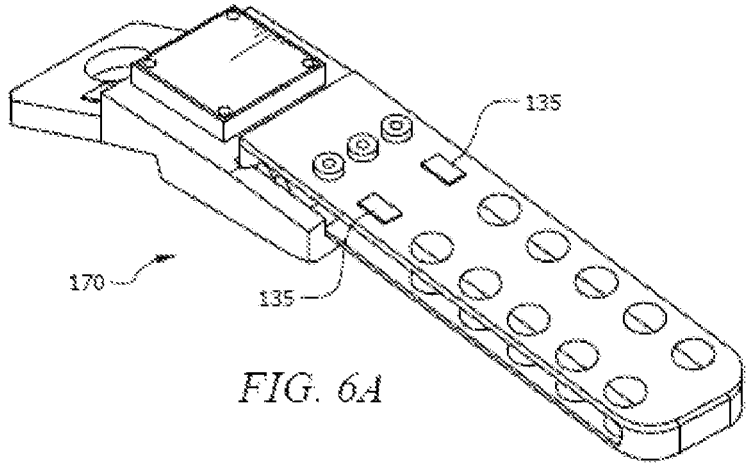
FIGS. 6A and B are views of a foot having toe and heel force sensing elements, according to an embodiment of the invention.
Figure 6B:
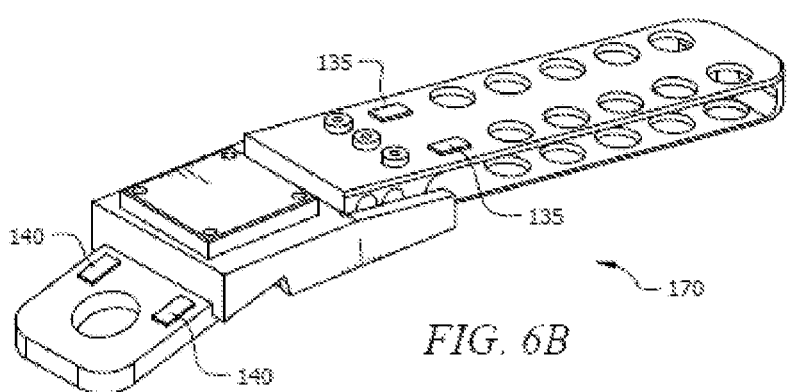

FIG. 6A is a view of a foot 170 having ball of foot sensors 135, according to an embodiment of the invention. Sensors 135 are provided to measure the ground reaction forces near the ball of the foot, such as when the foot strikes the ground. FIG. 6B is a view of a foot 170 having ball of foot sensors 135 and heel sensors 140, according to an embodiment of the invention. Sensors 140 are provided to measure the ground reaction forces on the heel of the foot when the foot 170 strikes the ground. Sensors 135 and 140 can be embodied as strain based sensors.

Unlike existing passive prostheses, the introduction of power into a prosthesis according to embodiments of the invention provides the ability for the device to also act, rather than simply react. As such, the development of a suitable controller and control methodology that provides for stable and reliable interaction between the user and prosthesis is provided herein. Control according to embodiments of the invention has been found to enable the user to interact with the prosthesis by leveraging its dynamics in a manner similar to normal gait, and also generates more stable and more predictable behavior.

Thus, rather than gather user intent from the joint angle measurements from the contralateral unaffected leg, embodiments of the invention infer commands from the user via the (ipsilateral) forces and moments of interaction between the user and prosthesis. Specifically, the user interacts with the prosthesis by imparting forces and moments from the residual limb to the prosthesis, all of which can be measured via suitable sensor(s), such as sensors 125, 140 and 141 described above which measures moments/forces. These forces and moments serve not only as a means of physical interaction, but also serve as an implicit communication channel between the user and device, with the user's intent encoded in the measurements. Inferring the user's intent from the measured forces and moments of interaction according to embodiments of the invention provides several advantages relative to the known echo approach.

In one embodiment of the invention the torque required at each joint during a single stride (i.e. a single period of gait) can be piecewise represented by a series of passive impedance functions. A regression analysis of gait data indicates that joint torques can be characterized by functions of joint angle ($\theta$) and angular velocity by an impedance model, such as the following exemplary passive impedance function shown in equation 1 below:

$$\tau = k_1(\theta - \theta_e) + b*\dot{\theta} \qquad (1)$$

where $k_1$, b, and the equilibrium joint angle $\theta_e$ are all constants that are generally generated empirically, and are constants for a given joint during a given internal phase (e.g. knee, internal phase 3). $k_1$ characterizes the linear stiffness, b is the linear damping coefficient, $\theta$ is the measured joint angle which can characterize the state of the prosthesis, $\theta_e$ is the equilibrium angle, $\dot{\theta}$ is the angular velocity of the joint, and $\tau$ is the joint torque. Given these constants, together with instantaneous sensor measurements for $\theta$ and $\dot{\theta}$ the torque ($\tau$) at the joints (knee and ankle) can be determined.

Figure 7:
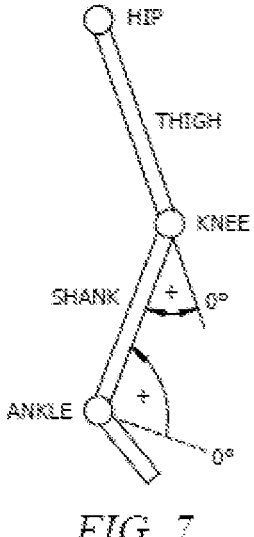
FIG. 7 shows the joint angle and torque convention used herein. Positive torque is defined in the direction of increasing angle.

Positive directions of the angle ($\theta$) and torque ($\tau$) as used herein are defined as shown in FIG. 7. If the coefficients b and $k_1$ are constrained to be positive, then the joints will each exponentially converge to a stable equilibrium at $\theta = \theta_e$ and $\dot{\theta} = 0$ within each internal phase. That is, within any given internal phase, the actuators are energetically passive (i.e. the joint will come to rest at a local equilibrium). While the unactuated prosthesis can be energetically passive, the behavior of one joint (knee or ankle) or the combined behavior of the knee and ankle joints, can be likewise passive, and thus will generally respond in a predictable manner.

Responsive to direct input from the user (e.g. a heel strike) to trigger a change in internal phase, power (torque) can be delivered from the power source (e.g. battery) to the prosthesis in the proper magnitude to provide the desired movement. Since the switching can be triggered by direct input from the user related to the current internal phase, the user maintains direct influence over the power applied to the prosthesis. If the user does not trigger the next internal phase (i.e. remains stationary) no net energy is delivered. That is, the prosthesis will generally cease to receive power from the power source for moving the joint, and will instead, due to the damped response, soon come to rest at the local equilibrium identified with the present internal phase.

As described above, the decomposition of joint behavior into passive segments requires the division of the gait cycle into a plurality of internal phases or "finite states" characterized by an impedance function and a set of constants for the impedance function, as dictated by their functions and the character of the piecewise segments of the impedance functions described above. The switching rules between internal phases should generally be well defined and measurable, and the number of phases should be sufficient to provide a substantially accurate representation of normal joint function. In one embodiment of the invention, the swing and stance phase of gait can constitute a minimal set of internal phases.

Figure 8:
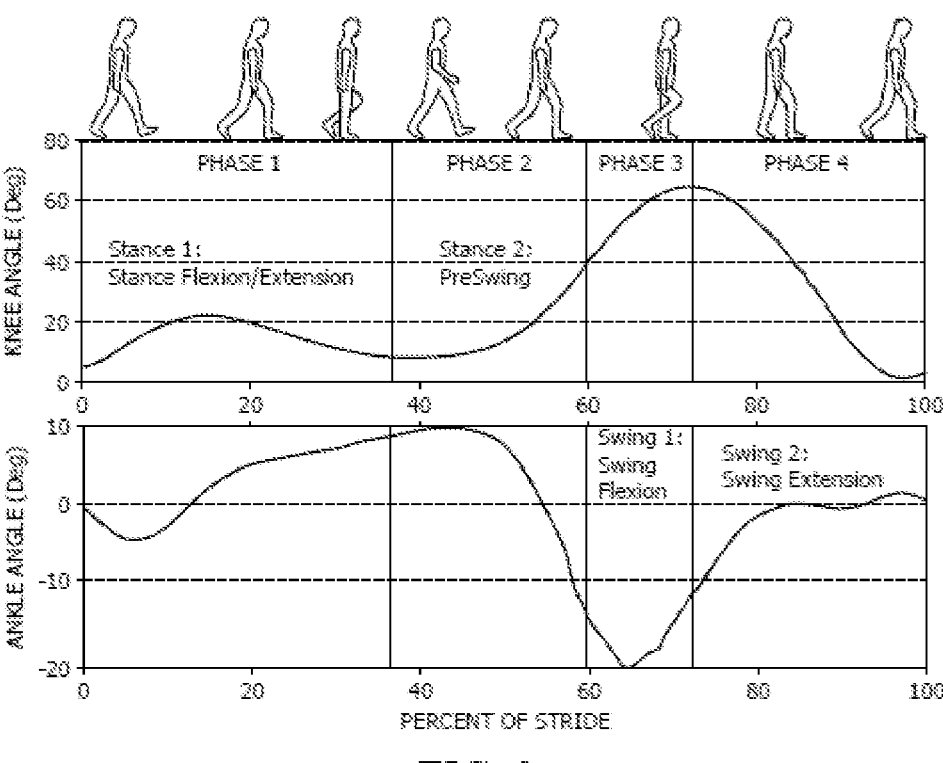
FIG. 8 shows the subdivision of normal walking into four internal phases showing the knee and ankle angles during the phases, according to an embodiment of the invention.

Based on least-squares regression fitting of Equation 1 to empirical gait data, the present Inventors determined that such fits were improved significantly by further dividing the two modes of swing and stance each into two additional internal phases to realize four phases, as shown in FIG. 8. A fifth internal phase can also be added, as illustrated in FIG.

16. The angle (θ) of the prosthetic knee (above) and ankle joint (below) can be provided during each internal phase as a function of the % of the stride. Angle values shown can be used as threshold values to trigger phase changes as described below relative to FIG. 9. As clear to one having ordinary skill in the art, the number of phases can be other than two or four.

Figure 9:
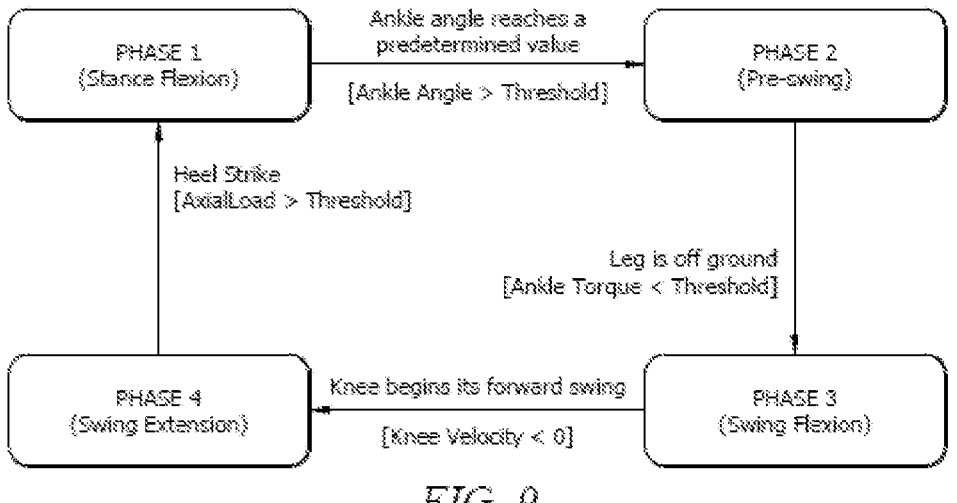
FIG. 9 shows a finite-state model of normal walking, according to an embodiment of the invention. Each box represents a different internal phase and the transition conditions between the internal phases are specified.
Figure 16:
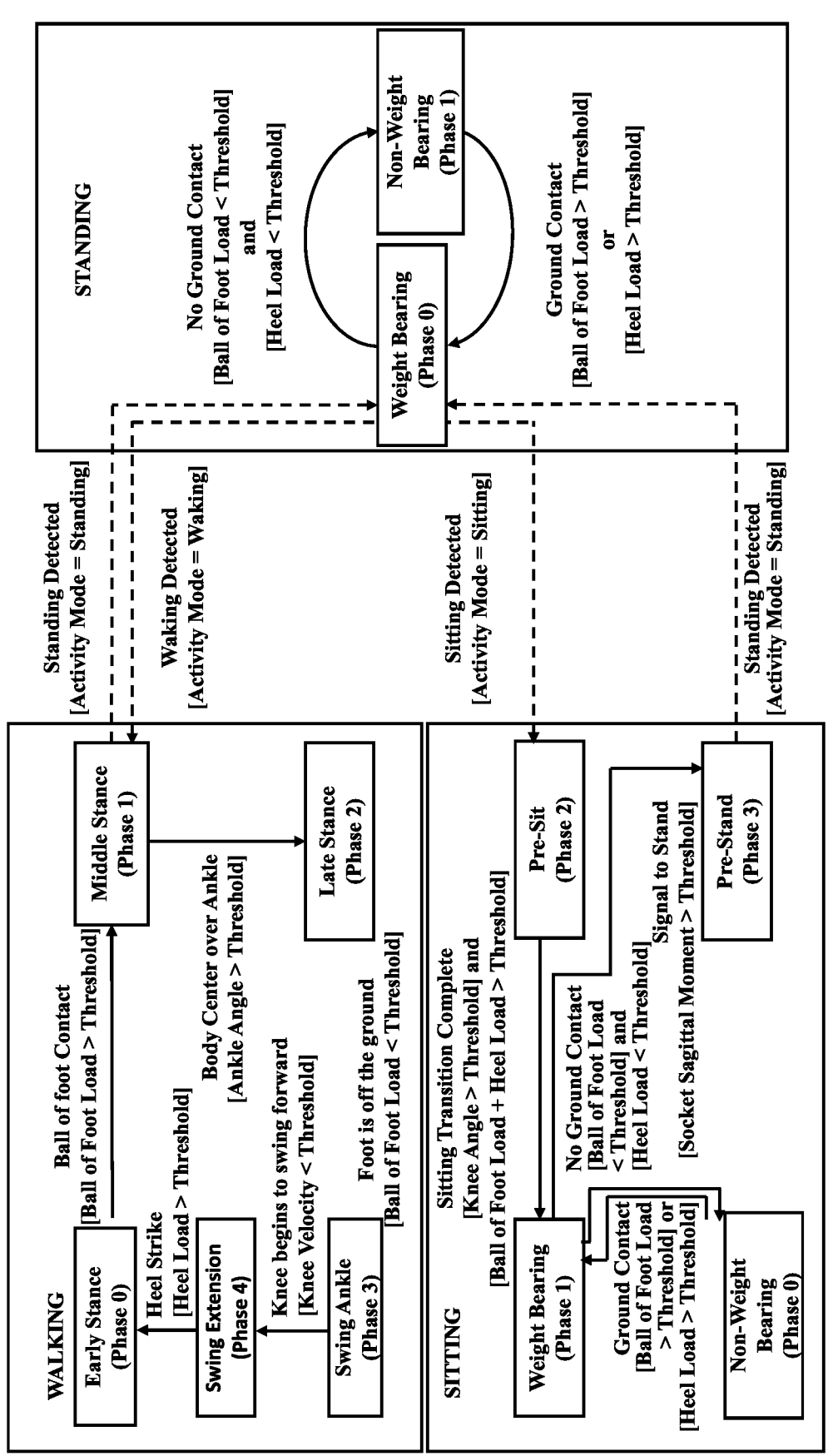
FIG. 16 is a control state chart for the three activity modes corresponding to walking, standing, and sitting, and for the internal phases and their corresponding transitions within each activity mode.

FIG. 9 shows exemplary switching rules between internal phases for walking. FIG. 16 shows another set exemplary switching rules, for walking, standing, and sitting activity modes. As described above, if the user does not initiate actions that trigger the next phase (e.g. based on the switching rules), the prosthesis will cease to receive power and will come to rest at the local equilibrium identified with the present phase. For example, switching can be based on the ankle angle >a threshold value (Mode 1 to Mode 2), or ankle torque <threshold) (Mode 2 to Mode 3), the angle or torque measurements provided by on board sensors as described above.

Phase 1 shown in FIG. 8 begins with a heel strike by the user (which can be sensed by the heel force sensor), upon which the knee immediately begins to flex so as to provide impact absorption and begin loading, while the ankle simultaneously plantarflexes to reach a flat foot state. Both knee and ankle joints have relatively high stiffness (and can be accounted for by k1 in equation 1) during this phase to prevent buckling and allow for appropriate stance knee flexion, because phase 1 comprises most of the weight bearing functionality. Phase 2 is the push-off phase and begins as the ankle dorsiflexes beyond a given angle (i.e. user's center of mass lies forward of stance foot). The knee stiffness decreases in this mode to allow knee flexion while the ankle provides a plantarflexive torque for push-off. Phase 3 begins as the foot leaves the ground as detected by the ankle torque load cell and lasts until the knee reaches maximum flexion. Mode 4 is active during the extension of the knee joint (i.e. as the lower leg swings forward), which begins as the knee velocity becomes negative and ends at heel strike (e.g. as determined by the heel force sensor).

In both of the swing phases (Phases 3 and 4), the ankle torque can be small and can be represented in the controller as a (relatively) weak spring regulated to a neutral position. The knee can be primarily treated as a damper in both swing phases.

Figure 10:
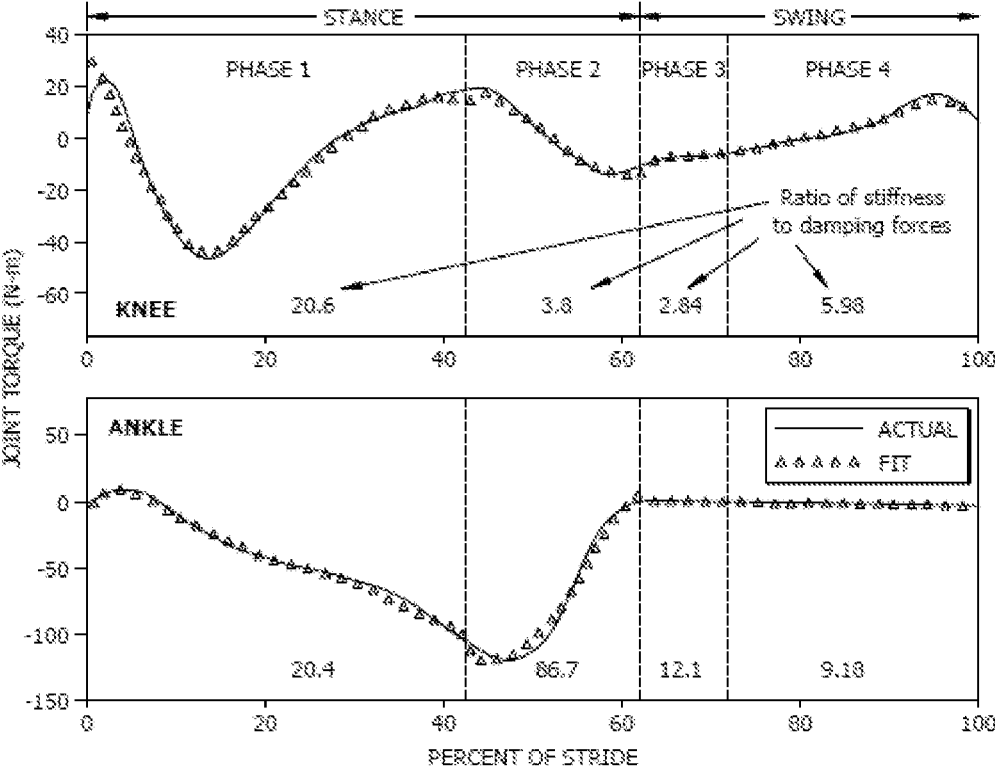
FIG. 10 shows piecewise fitting of knee and ankle torques during normal speed level walk scaled for a 75 kg adult to a non-linear spring-damper impedance model.

Impedance modeling of joint torques was preliminarily validated by utilizing the gait data from a healthy 75 kg subject, as derived from body-mass normalized data. Incorporating the four internal phases described above, along with the motion and torque data for each joint, a constrained least-squares optimization was conducted to generate a set of parameters $k_1$, b and $θ_e$, for each phase for each joint for use in Equation 1. The resulting parameter set can be fit to joint torques and is shown graphically in FIG. 10. FIG. 10 shows piecewise fitting of knee and ankle torques during normal speed level walk scaled for a 75 kg adult to a non-linear spring-damper impedance model. The numbers shown in each phase represent the mean ratio of the stiffness forces to damping forces predicted by the fit. The vertical lines represent the segmentation of a gait stride into four distinct phases. The fit shown in FIG. 10 clearly indicates that normal joint function can be represented by the use of piecewise passive functions.

Controllers according to embodiments of the invention generally comprise an underlying gait controller (intra-modal controller). An optional supervisory gait controller (also called intent recognizer) can also be provided. Both controllers generally utilize measured information. This information generally comprises user and ground interaction forces (F) and moments/torques (τ), joint angles and angular velocities from on-board sensors, and can be used to extract real-time input from the user. The gait control component utilizes the sensed instantaneous nature of the user input (i.e., moments and forces) to control the behavior of the leg within a given activity mode, such as standing, walking, or stair climbing.

Figure 11:
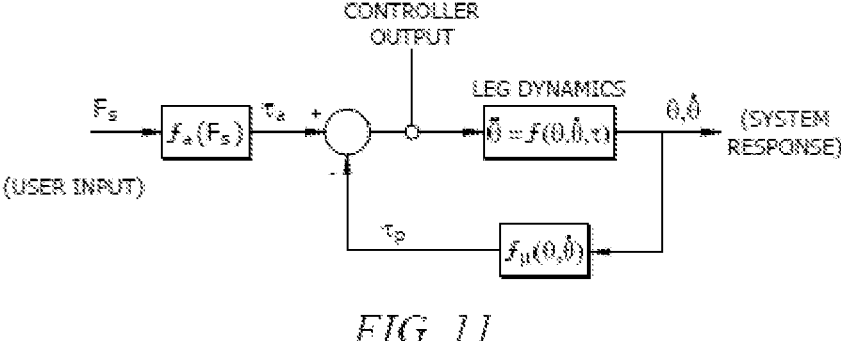
FIG. 11 is a diagram for an active/passive decomposition based control of the powered knee and ankle prosthesis, according to an embodiment of the invention.
Figure 12:
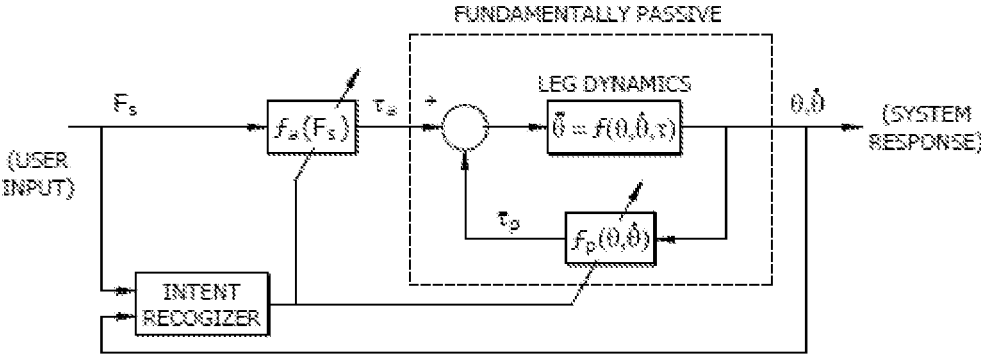
FIG. 12 is a diagram for a general form of active-passive decomposition control including intent recognition that provides supervisory modulation, according to an embodiment of the invention.

Two exemplary approaches to intra-modal impedance generation are described below. The first approach is shown in FIG. 11 and represents a general form of active-passive decomposition-based intra-mode control. The second embodiment shown in FIG. 12 includes the control structure shown in FIG. 11 but adds a supervisory intent recognizing controller to modulate the intra-modal control based on inputs from an intent recognition module. As shown in FIGS. 11 and 12, $F_s$ is the force the user of the prosthesis is applying, such as a heel force in the case of a heel strike, t represents joint torque, and θ represent joint angles. $τ_a$ represents the active component of joint torque which is roughly proportional to the input force, and $τ_p$ represents the passive component of torque. The active joint torque $τ_a$ is thus the total joint torque t minus the passive joint torque, $τ_p$. Derivatives are shown using the dot convention, with one dot being the first derivative (e.g., being angular velocity) and two dots representing the second derivative.

In the embodiment of the intra-modal controller shown in FIG. 11, the behavior of the prosthesis can be decomposed into a passive component and an active control component. The active control component is an algebraic function of the user's real-time input $F_s$ (i.e., sensed socket-prosthesis interface forces and moments and sensed ground reaction forces). The controller output is shown as the active torque ($τ_a$) minus the passive torque τp. The controller output $τ_a$–$τ_p$ applied to the prosthetic leg based on dynamics of the leg responds via θ and $\dot{θ}$. The system response, θ and $\dot{θ}$, is fed back to the controller.

Power applied to the prosthesis can be thus commanded directly by the user through measured interface forces and moments initiated by user movements. In the absence of these commands from the user, $F_s$=0, $τ_a$=0 and the prosthesis fundamentally (by virtue of the control structure) cannot generate power, and thus only exhibits controlled passive behavior. Due to the decomposition of energetic behaviors inherent in this control structure, the prosthesis under its own control can be generally stable and passive. Unlike known echo control approaches, the input can be real-time, based only on the affected leg, and thus the approach can be equally applicable to bilateral and unilateral amputees and can reflect the instantaneous intent of the user. Additionally, unlike echo control that is based on servocontrol, the prosthesis will exhibit a natural impedance to the user that should feel more like a natural limb. These combined features should result in an active prosthesis that will feel inasmuch as possible like a natural extension of the user. The structure and properties of both the gait controller and intent recognizer are described below.

As described above, since gait is largely a periodic activity, joint behavior can be functionally decomposed over a period by decomposing the joint torque into a passive component and an active component. The passive component can comprise a function of angle (i.e., single-valued and odd), and a function of angular velocity passive (i.e., single-valued and odd), such as equation 1 described above. The active component can be a function of the user input (i.e., socket interface forces). Given a set of data that characterizes a nominal period of joint behavior, the passive component can be first extracted from the whole, since the passive behavior is a subset of the whole (i.e., the passive component consists of single-valued and odd functions, while the active has no restrictions in form). The passive component can be extracted by utilizing a least squares minimization to fit a generalized singled-valued odd function of angle and angular velocity to the torque. Once the passive component is extracted, the residual torque (i.e., the portion that is not extracted as a passive component), can be constructed as an algebraic function of the sensed socket interface and ground reaction forces (i.e., the direct-acting user input) by incorporating a similar candidate function, but not restricted to be of passive form. Finally, superimposing the passive and active components provides a decomposed functional approximation of the original period joint torque.

In the embodiment of the intra-modal controller shown in FIG. 12, a supervisory intent recognizer can be added that utilizes the same sensed user inputs (i.e., moments and forces) as the intra-modal/gait controller, but extracts the user's intent based on the characteristic shape of the user input(s) and system response (e.g. F, θ, θ-dot). Based on the extracted intent, the supervisory intent recognizer modulates the behavior of the underlying gait controller to smoothly transition behavior within a gait (e.g., speed and slope accommodation) and between gaits (e.g., level walk to stair ascent), thus offering a unified control structure within and across all gaits.

Gait intent recognition can be a real-time pattern recognition or signal classification problem. The signal in this case is generally the combination of socket interface forces Fs and the dynamic state of the prosthesis, which in one embodiment can be a vector of the knee and ankle angles θ for a powered leg prosthesis according to an embodiment of the invention. A variety of methods exist for pattern recognition and signal classification including nearest neighbor algorithms, neural networks, fuzzy classifiers, linear discriminant analysis, and genetic algorithms.

Figure 14A:
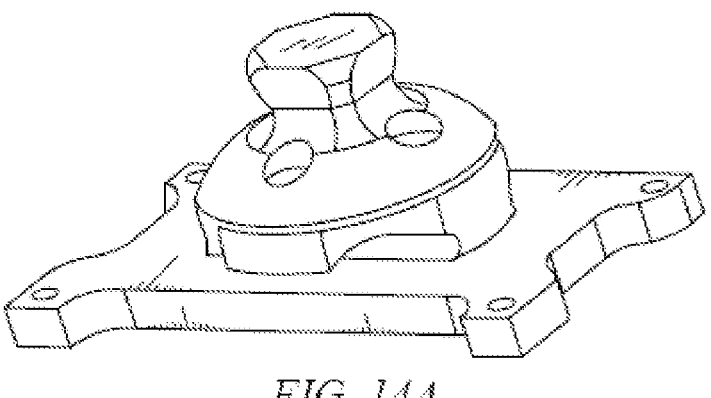
FIGS. 14A and 14B show perspective and bottom views of an exemplary sagittal moment load cell suitable for use in the various embodiments of the invention.
Figure 14B:
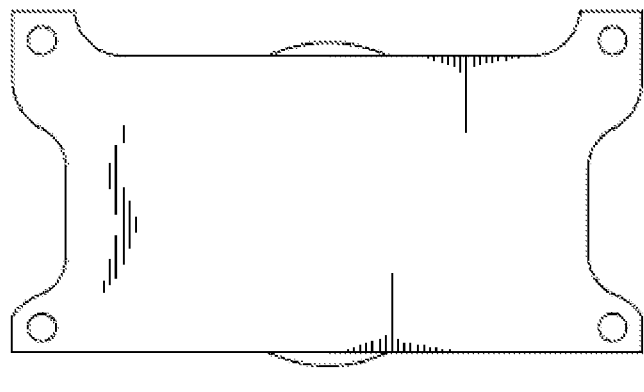
Figure 15:
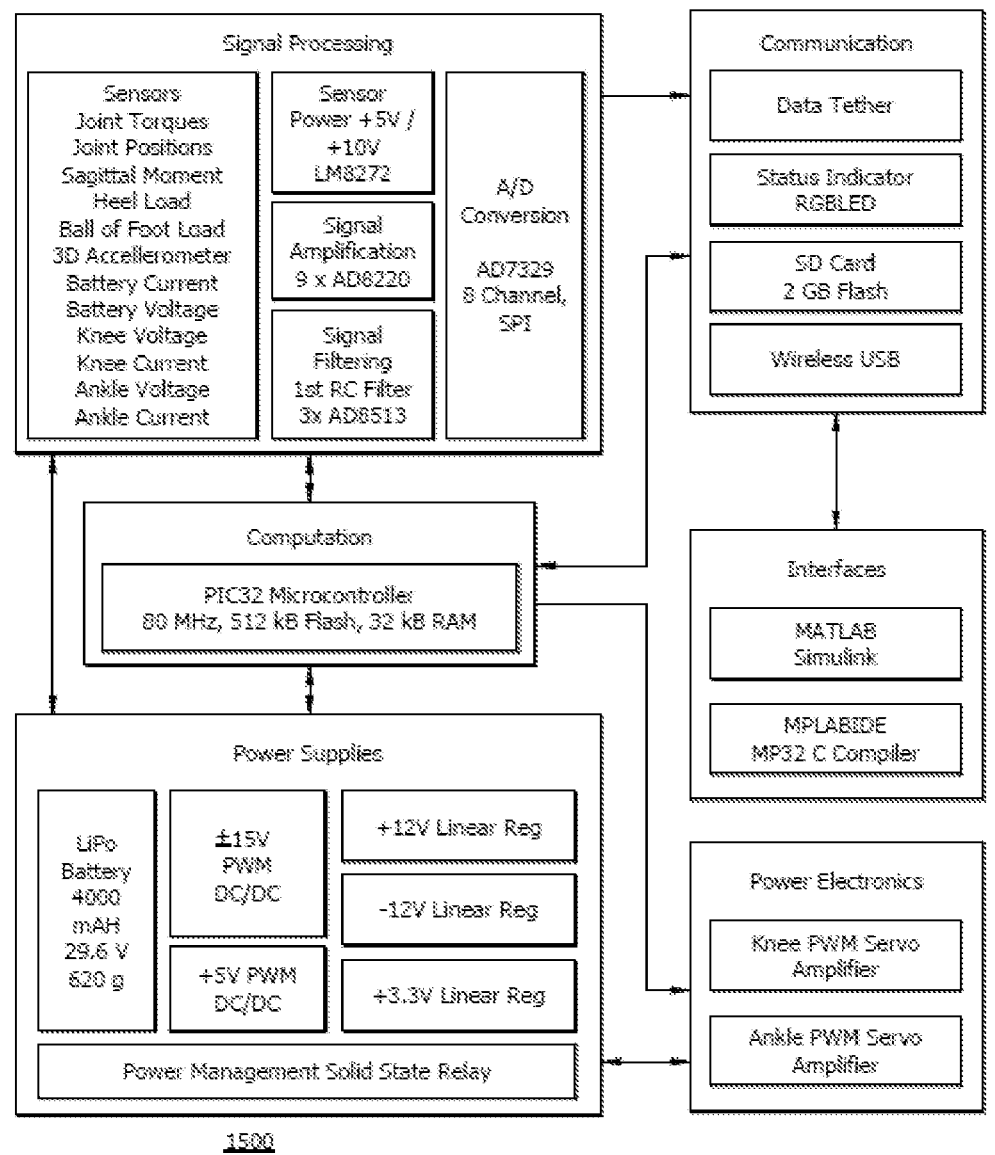
FIG. 15 is a block diagram of an exemplary embedded microcontroller in accordance with an embodiment of the invention.

As described above, embodiments of the invention include a number of sensors for providing signals for adjusting operation of a leg and ankle prosthesis. A description of one exemplary arrangement of sensors can be described below with respect to FIGS. 13A, 13B, 14A, and 14B. FIG. 13A is a side view of powered knee and ankle prosthesis 1300, according to another embodiment of the invention. FIG. 13B is a front view of powered knee and ankle prosthesis of FIG. 13A. FIGS. 14A and 14B show perspective and bottom views of an exemplary sagittal moment load cell suitable for use in the various embodiments of the invention.

Each joint actuation unit, such as knee actuation unit 1302 and ankle actuation unit 1304 in FIG. 13A, can include a uniaxial load cell positioned in series with the actuation unit for closed loop force control. Both the knee and ankle joints can incorporate integrated potentiometers for joint angle position. The ankle actuation unit can include a spring 1305, as described above with respect to FIGS. 1A-4. One 3-axis accelerometer can be located on the embedded system 1306 and a second one can located below the ankle joint 1308 on the ankle pivot member 1310. A strain based sagittal plane moment sensor 1312, such as sensor 1400 shown in FIGS. 14A and 14B, can located between the knee joint 1314 and the socket connector 1316, which measures the moment between a socket and the prosthesis. In the various embodiments of the invention, a sagittal plane moment sensor can be designed to have a low profile in order to accommodate longer residual limbs. The sensor can incorporate a full bridge of semiconductor strain gages which measure the strains generated by the sagittal plane moment. In one embodiment of the invention, the sagittal plane moment sensor was calibrated for a measurement range of 100 Nm. A custom foot 1318 can designed to measure the ground reaction force components at the ball 1320 of the foot and heel 1322. The foot can include of heel and ball of foot beams, rigidly attached to a central fixture and arranged as cantilever beams with an arch that allows for the load to be localized at the heel and ball of the foot, respectively. Each heel and ball of foot beam can also incorporates a full bridge of semiconductor strain gages that measure the strains resulting from the respective ground contact forces. In one embodiment of the invention, the heel and ball of foot load sensors were calibrated for a measurement range of 1000 N. In addition, incorporating the ground reaction load cell into the structure of a custom foot can eliminate the added weight of a separate load cell, and also enables separate measurement of the heel and ball of foot load. The prosthetic foot can be designed to be housed in a soft prosthetic foot shell (not shown).

The powered prostheses described above contain an embedded microcontroller that allows for either tethered or untethered operation. An exemplary embedded microcontroller system 1500 is shown in the block diagram in FIG. 15. The embedded system 1500 consists of signal processing, power supply, power electronics, communications and computation modules. The system can be powered by a lithium polymer battery with 29.6 V. The signal electronics require +/−12 V and +3.3 V, which are provided via linear regulators to maintain low noise levels. For efficiency, the battery voltage can be reduced by PWM switching amplifiers to +/−15 V and +5 V prior to using the linear regulators. The power can be disconnected via a microcontroller that controls a solid state relay. The power status can be indicated by LED status indicators controlled also by the microcontroller.

The analog sensor signals acquired by the embedded system include the prosthesis sensors signals (five strain gage signals and two potentiometer signals), analog reference signals from the laptop computer used for tethered operation, and signals measured on the board including battery current and voltage, knee and ankle servo amplifier currents and two 3-axis accelerometers. The prosthesis sensor signals are conditioned using input instrumentation amplifiers. The battery, knee motor and ankle motor currents are measured by current sense resistors and current sensing amplifiers. The signals are filtered with a first-order RC filter and buffered with high slew rate operational amplifiers before the analog to digital conversion stage. Analog to digital conversion can be accomplished by two 8-channel analog to digital convertors. The analog to digital conversion data can be transferred to the microcontroller via serial peripheral interface (SPI) bus.

The main computational element of the embedded system can be a 32-bit microcontroller. In the untethered operation state, the microcontroller performs the servo and activity controllers of the prosthesis and data logging at each sample time. In addition to untethered operation, the prosthesis can also be controlled via a tether by a laptop computer running MATLAB Simulink RealTime Workshop. In the tethered operation state, the microcontroller drives the servo amplifiers based on analog reference signals from the laptop computer. A memory card can be used for logging timestamped data acquired from the sensors and recording internal controller information. The memory chip can be interfaced to the computer via wireless USB protocol. The microcontroller sends PWM reference signals to two four quadrant brushless DC motor drivers with regenerative capabilities in the second and forth quadrants of the velocity/torque curve.

Figure 17:
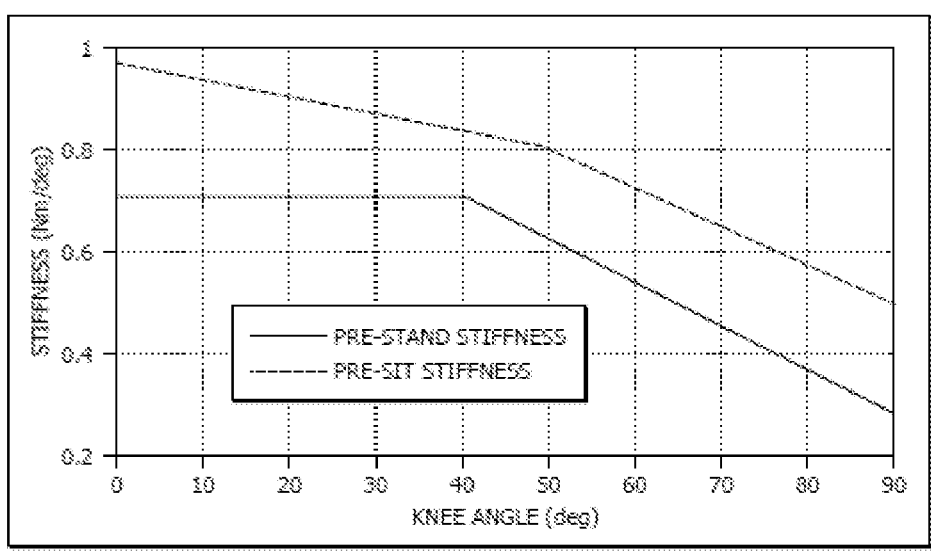
FIG. 17 shows knee angle modulated knee stiffness during pre-stand (solid line) and pre-sit (dashed line) phases.

As noted above with respect to FIG. 9, additional controls can be provided for operating the prosthesis when going from a sitting to a standing position or vice versa. This can be implemented via the use of a sitting mode controller implemented in the microcontroller. Operation of the sitting mode controller consists of four phases that are outlined in the general control state chart shown in FIG. 16. As shown in FIG. 16, two phases are primary sitting phases, weight bearing and non-weight bearing. The other two phases encompass the transition phases, pre-stand and pre-sit, for standing up and sitting down, respectively. Weight bearing and non-weight bearing are the primary sitting phases that switch the knee and ankle joints between high and low impedances, respectively. The transition phases, pre-stand and pre-sit, modulate the stiffness of the knee as a function of knee angle, as shown in FIG. 17, to assist the user in standing up and sitting down. FIG. 17 shows knee angle modulated knee stiffness during pre-stand (solid line) and pre-sit (dashed line) phases.

The modulation allows for smoother transitions near the seated position. The ankle joint can be slightly dorsiflexed with moderate stiffness during the standing up and sitting down phases. Switching between the four sitting phases occurs when sensor thresholds are exceeded, as depicted FIG. 16. The parameters of the impedance based controllers are tuned using a combination of feedback from the user and joint angle, torque and power data from the prosthesis.

In the various embodiments of the invention, actuation for a prosthesis can be provided by two motor-driven ball screw assemblies that drive the knee and ankle joints, respectively, through a slider-crank linkage. The prosthesis can be capable of 120° of flexion at the knee and 45° of planter-flexion and 20° of dorsiflexion at the ankle. In one embodiment, each actuation unit consists of a DC motor (such as a Maxon EC30 Powermax) connected to a 12 mm diameter ball screw with 2 mm pitch, via helical shaft couplings. An exemplary ankle actuation unit additionally incorporates a 302 stainless steel spring (51 mm free length and 35 mm outer diameter), with 3 active coils and a stiffness of 385 N/cm in parallel with the ball screw.

Figure 18:
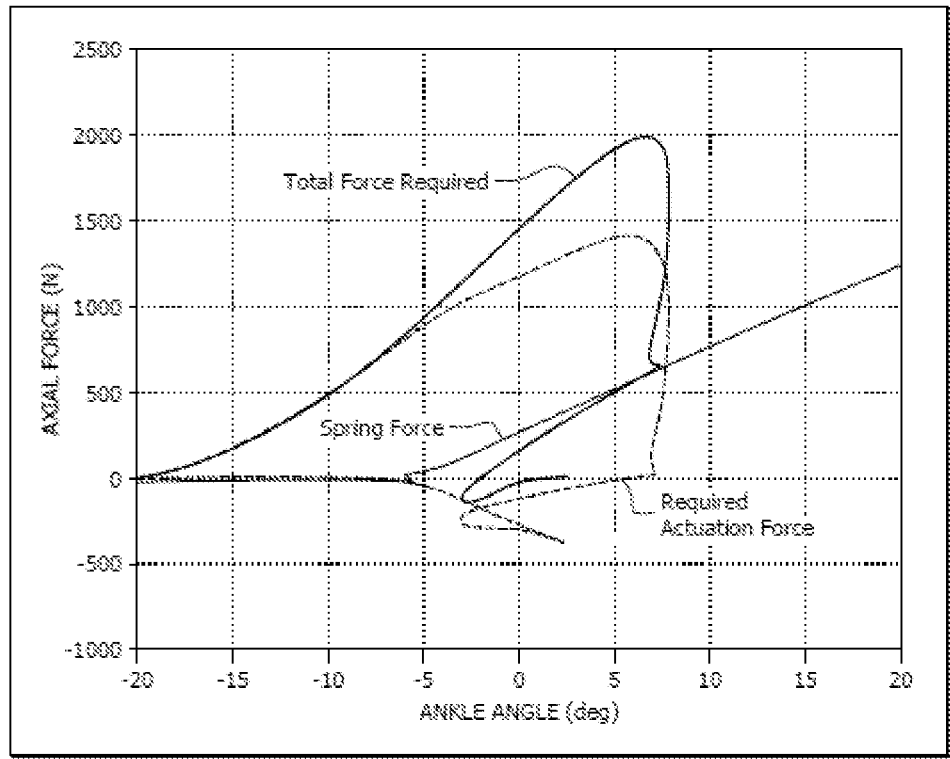
FIG. 18 is a plot of axial actuation unit force versus ankle angle.

As described above with respect to FIGS. 1A-4, the purpose of the spring can be to bias the motor's axial force output toward ankle plantarflexion, and to supplement power output during ankle push off. The stiffness of the spring can be maximized to allow for peak force output without limiting the range of motion at the ankle. The resulting axial actuation unit's force versus ankle angle plot can be shown in FIG. 18. FIG. 18 is a plot if axial force as a function of ankle angle illustrating spring force, actuator force and total force. FIG. 18 graphically demonstrates for fast walking the reduction in linear force output supplied by the motor at the ankle through the addition of the spring. Note that the compression spring does not engage until approximately five degrees of ankle plantarflexion. Each actuation unit can include a uniaxial load cell (such as Measurement Specialties ELPF-500L), positioned in series with the actuation unit for closed loop force control of the motor/ballscrew unit. Both the knee and ankle joints can incorporate bronze bearings and, for joint angle measurement, integrated precision potentiometers (such as an ALPS RDC503013). A strain based sagittal plane moment sensor, as previously described with respect to FIGS. 14A and 14B, can be located between the knee joint and the socket connector, which measures the moment between the socket and prosthesis. The ankle joint connects to a foot, which incorporates strain gages to measure the ground reaction forces on the ball of the foot and on the heel. The central hollow structure houses a lithium-polymer battery and provides an attachment point for the embedded system hardware. To better fit with an anthropomorphic envelope, the ankle joint can be placed slightly anterior to the centerline of the central structure. This gives the prosthesis the illusion of flexion when the amputee can be standing vertically with the knee fully extended.

The length of the shank segment can be varied by changing the length of three components; the lower shank extension, the spring pull-down, and the coupler between the ball nut and ankle. Additional adjustability can be provided by the pyramid connector that can be integrated into the sagittal moment load cell for coupling the prosthesis to the socket (as is standard in commercial transfemoral prostheses).

Passive joint torque, $\tau_p$, can be defined as the part of the joint torque, $\tau$, which can be represented using spring and dashpot constitutional relationships (passive impedance behavior). The system can only store or dissipate energy due to this component. The active part can be interpreted as the part which supplies energy to the system and the active joint torque can be defined as $\tau_a = \tau - \tau_p$. This active part can be represented as an algebraic function of the user input via the mechanical sensory interface (i.e socket interface forces and torques).

Figure 19:
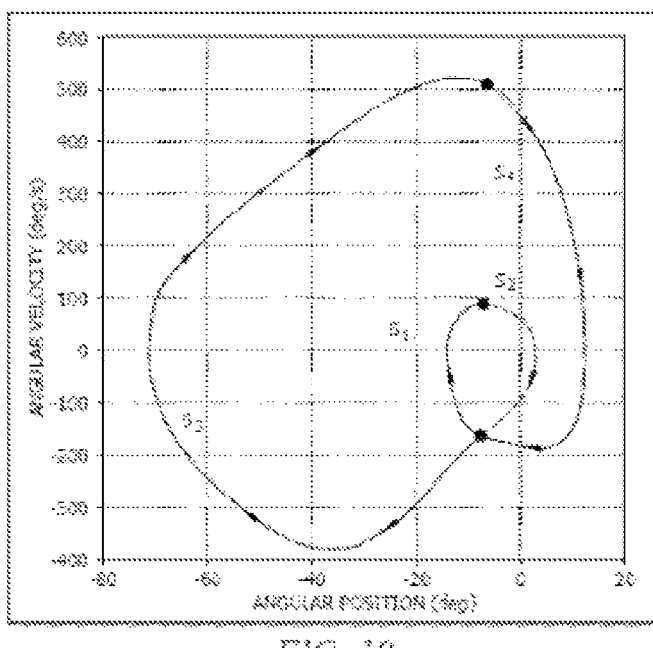
FIG. 19 shows a normal speed walking phase portrait of the knee joint and four stride segments.

Gait is considered a mainly periodic phenomena with the periods corresponding to the strides. Hence, the decomposition of a stride will give the required active and passive torque mappings for a specific activity mode. In general, the joint behavior exhibits varying active and passive behavior in each stride. Therefore, segmenting of the stride in several parts can be necessary. In this case, decomposition of the torque over the entire stride period requires the decomposition of the different segments and piecewise reconstruction of the entire segment period. In order to maintain passive behavior, however, the segments cannot be divided arbitrarily, but rather can only be segmented when the stored energy in the passive elastic element is zero. This requires that the phase space can only be segmented when the joint angle begins and ends at the same value. FIG. 19 shows the phase portrait of normal speed walking and the four different stride segments, $S_1$, $S_2$, $S_3$ and $S_4$. Thus, the entire decomposition process consists of first appropriate segmentation of the joint behavior, followed by the decomposition of each segment into its fundamental passive and active components.

Figure 20:
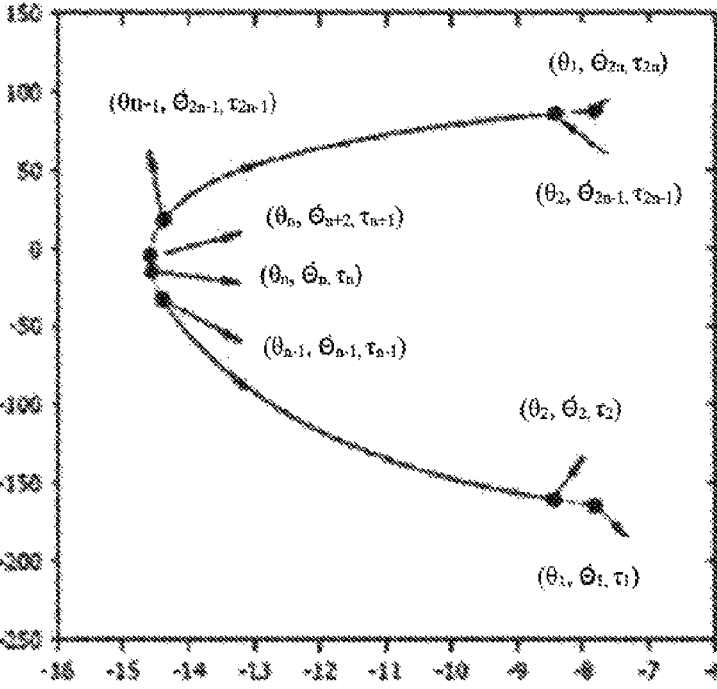
FIG. 20 shows the selection of indexing data samples during a first segment of a walking stride.

The decomposition of each segment shown in FIG. 19 can be converted to an optimization problem. In each segment of the stride, 2n data points are selected by sampling the angular position in equal intervals between its minimum and maximum and selecting the corresponding positive and negative angular velocities. In this work, the number of angular position samples for each segment, n can be set to be 100. The constrained least squares optimization problem given in Equation 2 below can be constructed and solved.

$$\min_x \frac{1}{2} \|Cx - d\|_2^2 \quad \text{s.t.} \quad 0 \le x \tag{2}$$

where C, x and d are defined in Equations 3, 4, and 5 below, respectively. The indexing of the joint angular position, angular velocity and moment samples are explained via the sketch in FIG. 20. FIG. 20 shows a selection and indexing of data samples from a first segment.

$$C_{4nx3n} = [\, C_1 \quad C_2 \quad C_3 \,]^T \tag{3}$$

$$C_1 = \begin{bmatrix} \left( \mathrm{diag}\left( \begin{bmatrix} \theta_1 \\ \theta_2 \\ \vdots \\ \theta_n \end{bmatrix}_{nx1} \right) -\alpha \right) \mathrm{diag}\left( \begin{bmatrix} \dot{\theta}_1 \\ \dot{\theta}_2 \\ \vdots \\ \vdots \\ \vdots \\ \dot{\theta}_n \end{bmatrix}_{2nx1} \right) \\ \mathrm{diag}\left( \begin{bmatrix} \theta_n \\ \theta_{n-1} \\ \vdots \\ \theta_1 \end{bmatrix}_{nx1} \right) -\alpha \end{bmatrix}_{2nx2n}$$

$$C_2 = \begin{bmatrix} C_{23} \\ C_{22} \quad C_{23} \end{bmatrix}_{2n-1x3n}$$

$$C_{21} = \begin{bmatrix} \theta_1 & -\theta_2 & \theta_1 & \dots & \theta_1 \\ 0 & \ddots & \ddots & \ddots & \vdots \\ \vdots & \ddots & \theta_{n-1} & \theta_n & 0 \\ 0 & \dots & 0 & 0 & 0 \end{bmatrix}_{nxn}$$

$$C_{22} = \begin{bmatrix} \theta_n & -\theta_{n-1} & 0 & \dots & 0 \\ 0 & \ddots & \ddots & \ddots & \vdots \\ \vdots & \ddots & \theta_3 & -\theta_2 & 0 \\ 0 & \dots & 0 & \theta_2 & -\theta_1 \end{bmatrix}_{n-1,xn}$$

$$C_{23} = \begin{bmatrix} \dot{\theta}_1 & -\dot{\theta}_2 & 0 & \dots & 0 \\ 0 & \ddots & \ddots & \ddots & \vdots \\ \vdots & \ddots & \dot{\theta}_{2n-1} & -\dot{\theta}_{2n-1} & 0 \\ 0 & \dots & 0 & \dot{\theta}_{2n-1} & -\dot{\theta}_{2n} \end{bmatrix}_{2n-1x2n}$$

$$C_3 = [\, \beta \quad \beta \quad \dots \quad \dots \quad \dots \quad \beta \quad \beta \,]_{1x3n}$$

$$x_{3nx1} = \begin{bmatrix} k_1 \\ k_2 \\ \vdots \\ k_{n-1} \\ k_n \\ b_1 \\ b_2 \\ \vdots \\ b_{2n-1} \\ b_{2n} \end{bmatrix} \tag{4}$$

$$d_{4nx1} = \begin{bmatrix} \tau_1 \\ \tau_2 \\ \vdots \\ \tau_{2n-1} \\ \tau_{2n} \\ \tau_1 - \tau_2 \\ \tau_2 - \tau_3 \\ \vdots \\ \tau_{2n-1} - \tau_{2n} \\ 0 \end{bmatrix} \tag{5}$$

The matrix C consists of three sub-matrices, $C_1$, $C_2$ and $C_3$. $C_1$ can be the main part responsible for the fitting of the spring and dashpot constants, k and b. $C_2$ bounds the rate of change of the passive joint torque and ensures smoothness in the resulting passive joint torque, and $C_3$ is basically a row of penalty constants, $\beta$, which penalizes large values of the spring and dashpot constants and thus limits the magnitudes of both. In this work, $\beta$ is set to 0.1.

The origin of each virtual spring can be also added to the optimization problem formulation as a parameter in order to obtain a tighter passive torque fit. Therefore, the optimization problem given by (3) can be solved iteratively for a range of values of spring origin constant, $\alpha$. The solution with the least error norm can be selected as the optimal solution.

Figure 21A:
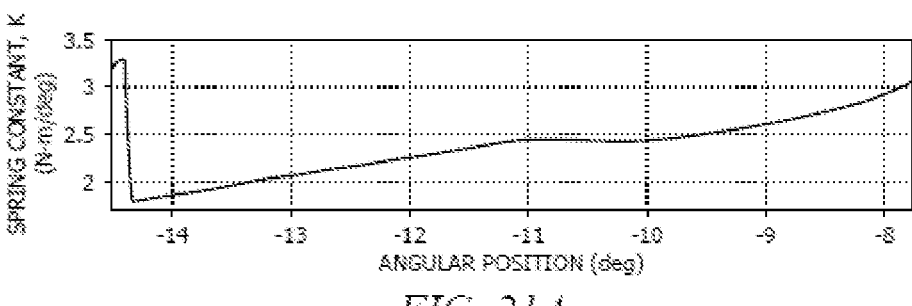
FIG. 21A is the output of the decomposition for Segment 1 showing the spring constants.
Figure 21B:
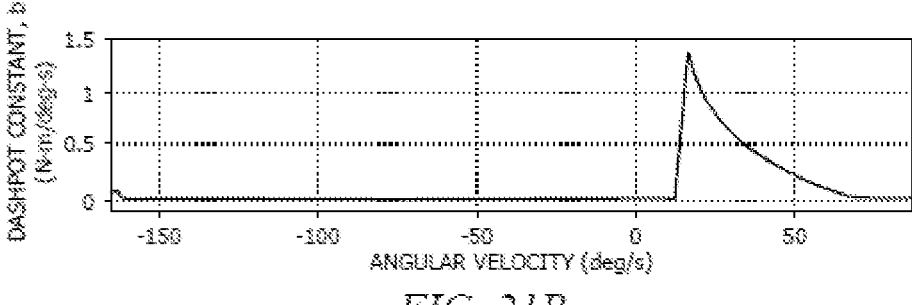
FIG. 21B is the output of the decomposition for Segment 1 showing the dashpot constants.
Figure 21C:
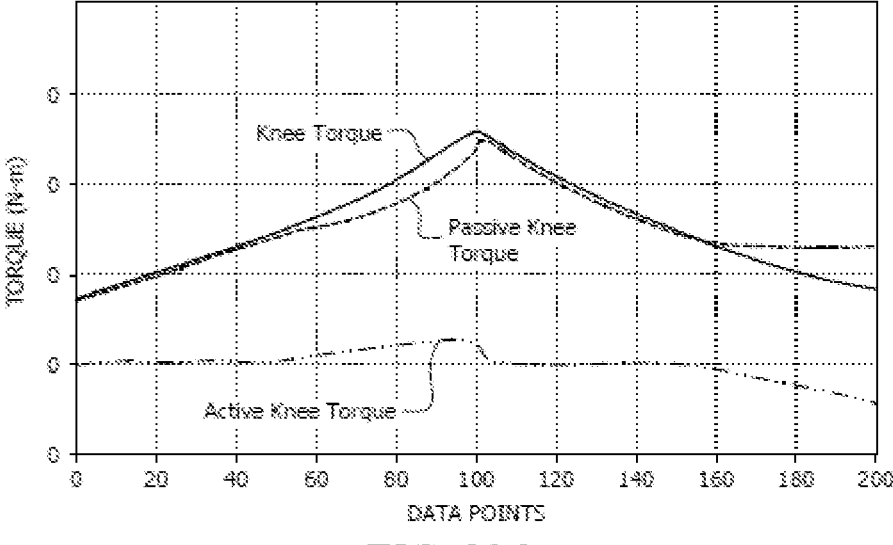
FIG. 21C is the output of the decomposition for Segment 1 showing the active and passive knee torques.
Figure 22:
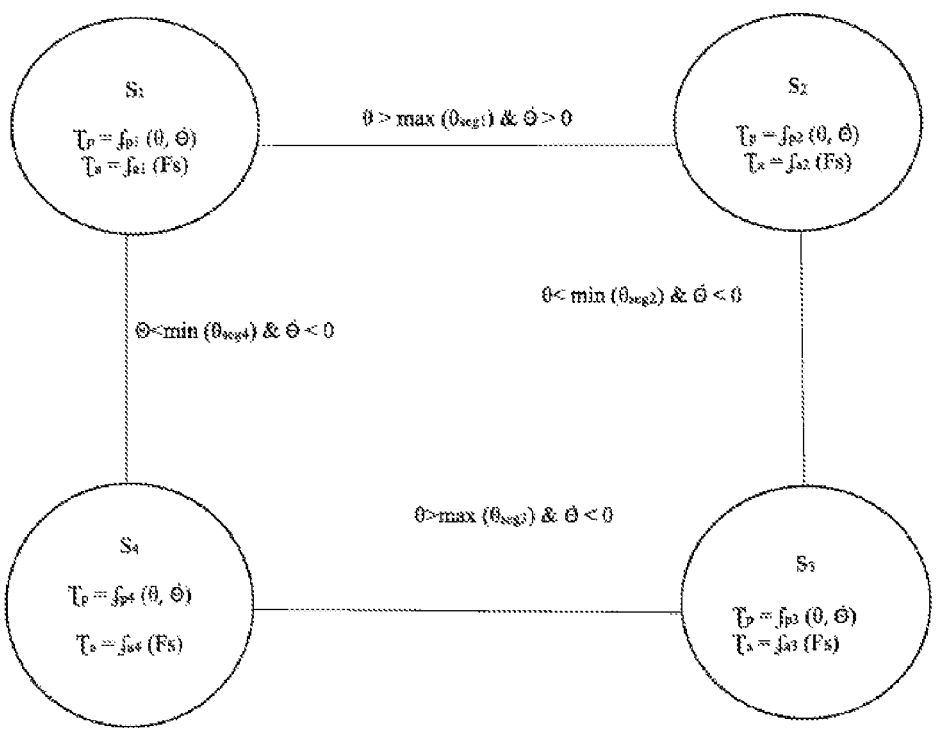
FIG. 22 is a state chart for governing the discrete dynamics of an active-passive decomposition controller in accordance with an embodiment of the invention.

The result of the above stated constrained optimization problem for segment 1 can be shown in plots (a), (b), and (c) in FIG. 21. FIG. 21 is the output of the decomposition for $s_1$ in FIG. 19 showing the spring and dashpot constants and the active and passive knee torques (Spring origin, $\alpha$ .is 23 degrees).

As can be seen from FIG. 21, the decomposed passive part can be very similar to the joint torque, and thus it can be stated that the behavior of the joint can be mainly passive. The result of the decomposition for the segment $S_i$ can be stored in $R_i$ of the form given in Equation 6.

$$R_i = [\theta\, \dot{\theta}\, \tau_{pas}\, F_{s1}\, F_{s2}\, \tau_{act}]_{2nx6} \tag{6}$$

where $$\tau_{pas} = C_1 x$$

The procedure presented above decomposes the joint torques into active and passive parts. The joint torque references for the control of the prosthesis are generated by combining this active and passive torques. There are two major challenges to be solved. Firstly, the correct motion segment must be selected. Secondly, after the motion segment is selected at each sampling instant a new joint torque reference can be generated using the discrete mappings for the active and passive torque parts.

A switching system modeling approach incorporating both discrete and continuous states can be used for the reconstruction of the torque reference signal. The state chart shown in FIG. 22. will govern the discrete dynamics of the controller. Since the sequence of the segments can be ordered (i.e., the direction of the motion for a specific gait phase does not change), each segment can transition only to the next one, where the transition guard function can be written as a inequality in terms of $\theta$ and $\dot{\theta}$. The transitions between segments take no time and the dynamics of the controller are governed by the $\{f_{pi}(\theta, \dot{\theta}); f_{ai}(F_s)\}$ pair at each sampling instant. The joint reference torque is $$\tau_{ref} = \tau_a + \tau_p = f_{p_i}(\theta, \dot{\theta}) + f_{a_i}(F_S) \tag{7}$$

The decomposition algorithm presented above gives the result matrix, R, for each segment. The discrete data in R can be used to construct the joint torque reference for the continuous measurements of another trial in the same gait phase. At each sampling instant of the algorithm, the measurement vector $m=[\theta_m, \dot{\theta}_m, F_{S1\_m}, F_{S2\_m}]^T$ can be acquired. For the reconstruction of the passive knee torque part, the Euclidian error norm between the $[\theta_m\, \dot{\theta}_m]^T$ and the angular position and velocities of all the samples in that segment $[\theta_i\, \dot{\theta}_i]^T$ can be calculated as shown in Equation 8 and stored in the vector e.

$$e_i = \sqrt{(\theta_m - \theta_i)^2 + (\dot{\theta}_m - \dot{\theta}_i)^2} \tag{8}$$

Then two elements of this vector with the least error norm are found and the passive knee torque reference can be found as a weighted linear combination of the passive knee torques corresponding to these points. The reconstruction of the active knee torque part is similar where only $\{\theta, \dot{\theta}, \tau_{pas}\}$ is exchanged with $\{F_{S1}, F_{S2}, \tau_{act}\}$.

The supervisory controller (intent recognizer) switches among different underlying intramodal controllers depending on the activity mode the user imposes on the prosthesis. The intent recognizer consists of three parts: activity mode recognizer, cadence estimator and the slope estimator.

The activity mode recognizer detects the activity mode of the prosthesis (standing, walking, sitting, stair ascent or stair descent, etc . . . ). This can be accomplished by comparing the features which are generated in real time to a feature database using some machine learning and/or pattern recognition methods. The present implementation of the gait mode recognizer, which recognizes standing and walking modes, is described below.

Firstly, a database which contains all the possible activity modes (standing and walking in this case) can be generated by making experimental trials. In the experimental trials, the user can be asked to walk or stand in different controller modes for 50 second long trials. The socket sagittal moment above the knee joint, foot heel load, foot ball load, knee angle, knee velocity, ankle angle and ankle velocity are recorded with 1 ms sampling period. It should be noted that other sensor signals such as accelerations and electromyography measurements from the residual limb can be added to the list of the signals used for intent recognition. For example, from the recorded experimental trials, 10000 random frames (5000 standing and 5000 walking) of 100 samples length are generated for all the seven recorded signals. The mean and the standard deviation of each frame are computed. The mean and standard deviation of signals are selected as the features since minimal computation can be required to obtain them. A database containing 10000 samples with 14 features (mean and standard deviation of the seven signals) belonging to two classes (standing and walking) can be generated. After the database is generated, the dimension of the database can be reduced from 14 to three using principal component analysis (PCA). Dimension reduction can be necessary because pattern recognition for high dimensional datasets can be computationally intensive for real-time applications. After dimension reduction step, the standing and walking data can be modeled with Gaussian mixture models. Gaussian mixture models represent a probability distribution as a sum of several normal Gaussian distributions. The order of the Gaussian mixture model for each mode can be determined according to the Minimum Description Length Criteria.

As described above, the database generation, dimension reduction and the Gaussian mixture modeling are explained. For real-time decision making, overlapping frames of 100 samples can be generated at each 10 ms interval. 14 features described above are extracted from these frames and the PCA dimension reduction can be applied to these features to get a reduced three dimensional feature vector. The reduced dimension features can be fed to the Gaussian mixture models for standing and walking and the probability of the sample vector being standing or walking can be computed. The mode with the greater probability is selected as the instantaneous activity mode. Since one decision might give wrong results in some cases due to noise, disturbance, etc . . . , a voting scheme can be used to enhance the results. In the voting scheme, the controller activity mode is switched if and only if more than 90 percent of the instantaneous activity mode decisions among the last 40 decisions are a specific activity mode. Once a new activity mode is selected by the voting scheme, the underlying activity controller can be switched to the corresponding mode.

Such an activity mode recognizer is provided by way of illustration and not as a limitation. In the various embodiments of the invention, one or more parts of the algorithm might be modified. For example, in some embodiments, different features such as mean, max, kurtosis, median, AR coefficients, wavelet based features, frequency spectrum based features of the frame might be generated. Additionally, different dimension reduction techniques such as linear discriminant analysis, independent component analysis might be employed. Furthermore, different classification methods such as artificial neural networks, support vector machines, decision trees, hidden Markov models might be used.

Cadence estimation is accomplished by observing peak amplitudes in characteristic signal data and then measuring the time between successive peaks. Since walking is a cyclic activity each of the sensor signals will be periodic of cadence. The most relevant sensor signals will contain only one characteristic amplitude peak per stride such as foot heel load and the ball of foot load. In the real-time implementations, cadence estimation is accomplished by recording the foot load after heel strike when it exceeds 400 N until the load decreases below 350 N. Then, the time of occurrence of the peak load in this window is found and the previous peak time is subtracted from the new peak time. This corresponds to stride time and can be converted to cadence (steps/min) by multiplying with 120. Once the cadence is estimated, the intent recognizer selects the corresponding middle layer controller based on some predefined thresholds as in FIG. 23.

For example, in some embodiments, a 3D accelerometer capable of measuring ±3 g accelerations is embedded into the ankle joint coupler where the prosthetic foot is connected. An exemplary arrangement of such a system is shown by the schematic in FIG. 24. The accelerometer measurements are used to estimate the ground slope. In order to estimate the ground slope, the accelerometer data in tangential direction is used. Assuming the foot is flat on the ground, the ground slope angle, $\theta_s$, can be calculated as in equation (9) below.

$$\theta_s = \sin^{-1}\left(\frac{a_t}{g}\right) \tag{9}$$

In Eqn. 9, g is the gravitational constant. In order to find the ground slope estimate, $\hat{\theta}_S$, the accelerometer data should be collected while the foot is flat on the ground as determined by the heel and ball of the foot load sensors. While the foot is flat on the ground, equation (1) is computed for the frame of the collected data and the mean of this frame is outputted as the ground slope estimate, $\hat{\theta}_S$. Once the slope is estimated, the intent recognizer selects the corresponding middle layer controller based on some predefined thresholds. An exemplary state chart for such an intent recognizer is shown in FIG. 25.

Rather than a ballscrew and slider crank embodiment for the transmission of torque from a motor to the ankle and/or knee units, in some embodiments of the invention, the prosthesis can incorporate a friction and cable drive transmission embodiment. FIGS. 26A and 26B show front and back views of an exemplary embodiment of a friction drive transmission 2600 in accordance with an embodiment of the invention. As shown in FIGS. 26A and 26B, the shaft 2602 of an electric motor 2604 is preloaded against a first stage in a housing 2606, such as a larger diameter cylinder or friction drive gear 2608, which creates sufficient friction to transmit torque without slip. The shaft 2602 can use one or more friction rollers 2610 to transmit the torque. The first stage of the friction drive can also be supplemented with a second stage. The friction drive gear 2608 drives a smooth pinion 2612 directly, which is preloaded against a larger diameter cylinder or cable gear output 2614 in the housing 2606, which in turn transmits torque directly to the knee or ankle joint.

In addition to, or rather than a friction drive, the first or second stage of the transmission can alternatively be embodied by a cable drive transmission, in which a cable is wrapped around the circumference of a larger diameter cylinder, such as friction drive gear 2608, and also around the circumference of a smaller diameter cylinder, such as pinion 2612. In such embodiments, the cable is affixed to the friction drive gear 2608, and is pretensioned, using a tensioning screw 2616 or similar means, around both the drive gear 2608 and pinion 2612, such that friction between cable and pinion 2612 enables the transmission of torque from between the pinion 2612 and drive gear 2608. In one embodiment of a combined friction drive/cable drive transmission can be used, in which a first stage of the transmission (i.e., the friction drive gear 2608 connected directly to the electric motor 2604) is of the friction drive type, while the second stage of the transmission (i.e., the cable gear output 2614 connected directly to the knee or ankle joint) is of the cable drive type.

Rather than the ballscrew and slider crank or the friction drive and cable drive embodiments for the transmission of torque from a motor to the ankle and/or knee units, in some embodiments of the invention, the prosthesis can incorporate a chain drive or a belt drive transmission embodiment for implementing one or more stages of a transmission.

Advantages of a belt or chain drive approach over the ballscrew approaches described above include the ability to provide a fully enclosable/sealable (without need for a bellows-type cover) powered leg device. This facilitates component immersion in lubricating environment, and well as facilitating isolation from dirt, water, and other debris. As a result, this can extend the lifetime of transmission components. Another advantage of such a configuration is that it enables a greater range of motion of joint actuation, as opposed to a slider-crank mechanism (as used in a ballscrew configuration), which is generally limited. Further, the belt or chain drive approach also allows the device to maintain a constant transmission ratio throughout range of motion, which is not generally possible in the slider-crank mechanism typically used in a ballscrew configuration. Additionally, advantages of a belt or chain drive approach is that it maintains constant mechanism geometry throughout range of motion, belt and chain drive components are typically less expensive than ballscrew components, and belt and chain drive systems are typically characterized by lower audible noise than ballscrew configurations.

FIG. 27 shows an exemplary embodiment of a belt drive transmission 2700 in accordance with an embodiment of the invention. As shown in FIG. 27, a stage of the transmission 2700 can be embodied as a belt drive transmission, in which a belt 2702 is wrapped around the circumference of a larger diameter shaft, such as a first belt gear or pulley 2704, and also around the circumference of a smaller diameter shaft, such as second belt gear or pulley 2706. In such embodiments, the belt 2702 can be tensioned, using a tensioning device 2708. In one embodiment, the tensioning device 2708 can consist of a swing arm 2710, an additional pulley 2712 attached to the end of swing arm 2710, and tensioning screw 2714 for adjusting the swing arm 2710 to bias the additional pulley 2712 against the belt 2702, such that friction between the belt 2702 and belt gears 2704 and 2706 enables the transmission of torque from between second belt gear 2706 and first belt gear 2704. However, any other type of tensioning device can be used in the various embodiments to tension the belt 2702. For example, in some embodiments, the tensioning device 2708 can be a spring loaded device to automatically bias a pulley 2706 or other object against belt 2702 to cause the necessary tension.

It is worth noting that although transmission 2700 is illustrated in terms of a V-belt embodiment, the invention is not limited in this regard and can be used with any type of belts. For example, the belt 2702 can also be embodied as a flat belt, a round belt, a multi-groove belt, a ribbed belt, and a toothed or cog belt, to name a few. Further, the belt gears 2704 and 2706 can be configured in accordance with the type of belt being used.

In some embodiments, rather than utilizing a belt-based drive, a chain-based drive can be provided. The configuration in such embodiments can be substantially similar to that shown in FIG. 27. That is, a chain can be provided in place of belt 2702 and gears 2704 and 2706 can be embodied as sprockets compatible with the chain. In such embodiments, the tensioning device 2708 described above can still be utilized to maintain proper tension of the chain to enable the transmission of torque from between sprockets in the transmission.

In some embodiments, instead of utilizing a tensioning device as described above with FIG. 27, a pulley or sprocket can be configured with an eccentric mount. That is, configuring at least one of the drive gears in the transmission to allow an adjustment of its position. This is illustrated below with respect to FIGS. 28A-28D.

FIGS. 28A and 28B show side views of first and second positions, respectively, achievable for an exemplary embodiment of a chain drive transmission 2800 including an eccentric mount in accordance with an embodiment of the invention. Similar to the transmission described above with respect to FIG. 27, transmission 2800 includes a first shaft 2802 with first drive gears or sprockets 2804 and a second shaft 2806 with second drive gears or sprockets 2808 which can be coupled together via chains 2810 to transmit torques between sprockets 2804 and sprockets 2808. Although FIGS. 28A and 28B show that the transmission of torque between sprockets 2804 and sprockets 2808 is performed using two sets of sprockets (and thus using two chains), the embodiments are not limited in this regard. Rather, any number of chains can be used in the various embodiments.

As shown in FIGS. 28A and 28B, the first shaft 2802 is shown as including an additional sprocket 2812 for driving first shaft 2802. Such a configuration can be used when multiple drive stages are provided. However, the various embodiments are not limited in this regard.

In transmission 2800, the first shaft 2802 is configured to be eccentric. That is, the position of the first shaft 2802 is adjustable relative to the position of the second shaft 2806 so as to adjust the lateral separation between the shafts (i.e., to provide $d_A \neq d_B$). Accordingly, this also provides a means to adjust the tension in a chain (or a belt) between the first shaft 2802 and the second shaft 2806. To provide the eccentric mount, the first shaft 2802 can be mounted in a leg device to an adjustable bearing mount 2814. The operation and configuration of an exemplary embodiment of the adjustable bearing mount 2814 is illustrated with respect to FIG. 29.

FIG. 29 illustrates schematically the components for the adjustable bearing mount 2812. As shown in FIG. 29, the adjustable bearing mount 2814 can include a top plate 2902 to which first shaft 2802 is attached, a bottom plate 2904, bearings 2906 between the top plate 2902 and the bottom plate 2904, and fasteners 2908. These components of the adjustable bearing mount 2814 can be disposed within an enclosure 2910.

In FIG. 29, the fasteners 2908 are shown as screws or bolts. However, the various embodiments are not limited to any particular bearing type or design of screws or bolts and other bearing types or designs can be used without limitation. Further, the various embodiments are not limited to screws or bolts and any other type of removable fastener can be used without limitation. Additionally, FIG. 29 shows bearings 2906 as a collection of ball bearings disposed between plates 2902 and 2904. However, the various embodiments are not limited to any particular bearing type or design and other bearing types or designs can be used without limitation.

In operation, the enclosure 2910 can be configured such that when fasteners 2908 are loosened or removed, the bearings allow the top plate 2902 can be repositioned relative to the bottom plate 2904 via bearings 2906. Thus, when fasteners 2908 are replaced and tightened, the plates 2902 and 2904 are biased against bearings 2906 to prevent further motion of the top plate 2902 relative to the bottom plate 2904.

Such a configuration allows adjustment of the position of first shaft 2802. For example, this can allow the first shaft 2802 to transition between a first position, as shown in FIG. 28A, in which a chain or belt 2810 with reduced tension is provided, due to a reduced distance ($d_A$) between first shaft 2802 and second shaft 2806, to a second position, as shown in FIG. 28B, in which a chain or belt 2814 with increased tension is provided, due to an increased distance ($d_B$) between first shaft 2802 and second shaft 2806. However, the various embodiments are not limited to solely first and second positions. Rather, in the various embodiments, the adjustable bear mount 2812 can be configured to allow a variety of positions for the first shaft 2806 relative to the second shaft 2806.

An exemplary configuration of a powered leg prosthesis 3000 in accordance with the discussion above is illustrated schematically in FIG. 30. As shown in FIG. 30, the powered leg prosthesis 3000 includes a shank 3002 with a powered knee joint 3004 and a powered ankle joint 3006. The powered knee joint 3004 includes a socket interface 3008 for attaching a socket 3010 or other device for attachment of the powered leg prosthesis 3000 to an amputee. The powered ankle joint 3006 can have a foot portion 3012 attached thereto.

The shank 3002 can consist of a single, discrete unit. However, in some embodiments, the shank can include an upper portion 3014 and a lower portion 3016. Such a configuration allows the insertion of at least one extension unit 3018 to allow the length of the shank 3002 to be customized for the amputee.

Within each of the upper portion 3014 and the lower portion 3016, a belt or chain drive system can be implemented, as described above with respect to FIGS. 27-29. For example, as shown in FIG. 30, the upper portion 3014 can include a first motor 3022, a first upper drive stage 3024, and a second upper drive stage 3026 for providing power at the powered knee joint 3004. Similarly, the lower portion 3016 can include a second motor 3028, a first upper drive stage 3030, and a second upper drive stage 3032 for providing power at the powered ankle joint 3006. Each stage can consist of the belt or chain drive stage. Additionally, each stage can be configured to include an eccentric mount, such as mounts 3034 and 3036, to adjust tension in the upper portion 3014 and lower portion 3016 respectively.

In addition to the components described above, the powered prosthetic leg 3000 can include other components not illustrated in FIG. 30 for purposes of clarity. For example, the powered prosthetic leg can include a control system or device, as previously described, and one or more sensors throughout the powered prosthetic leg, also as previously described. Thus control of the powered prosthetic leg 3000 can occur insubstantially the same manner as described above.

Running Controller

Now that the configuration and operation of an exemplary lower limb device (a single powered prosthesis) has been described, the disclosure now turns to a description of the running controller in accordance with the various embodiments. It should be noted that the examples and results are presented below are provided solely for illustrating the various embodiments and are not intended to limit the various embodiments in any way.

I. Running Controller Considerations

A bipedal running gait is fundamentally distinct from a bipedal walking gait by the fact that, in the former, each foot is in the air more often than on the ground, while in walking, each foot is on the ground more often than in the air. In particular, the amount of time each foot is on the ground is referred to as the "stance" phase of gait. In walking, each leg remains in the stance phase for approximately 60% of the time, while in a bipedal running gait, each leg is in stance phase approximately 40% of the time. Assuming the two legs in a bipedal gait are completely out of phase, if each is in stance 40% of the time, then it follows that both must be in the air approximately 20% of the time, which can be referred to as the flight phase of running. In contrast, in walking, both feet are on the ground 20% of the time, which is referred to as the double-support phase of walking.

In order to sustain a flight phase in running, an amount of vertical propulsive energy must be produced by each leg at least equal to the amount of energy absorbed by the respective leg during the stance phase. Specifically, the stance phase of a running gait consists essentially of two phases: an absorption phase, which lasts roughly for the first half of the stance phase, and a propulsion phase, which lasts roughly for the second half of the stance phase. In the absorption phase, the knee and ankle joints function synchronously to absorb energy as the foot lands on the ground (called foot strike). During this absorption phase, the center of mass of the body is decelerated as it is lowered from the flight phase of the running gait. The absorption phase is followed by the propulsion phase, in which the knee and ankle joints synchronously generate power, which accelerates the center of mass of the body upward to set up the flight phase of the running gait.

In contrast, in a walking gait, the knee and ankle joints are not characterized by synchronous power absorption and generation. In particular, the ankle is characterized by absorption of a small amount of energy (relative to running) during most of the stance phase, followed by a generation of energy (a propulsion phase) similar to a running gait. The knee joint, however, behaves essentially passively. Specifically, the knee absorbs energy immediately following heel strike, but is characterized by energy absorption rather than generation during the latter period of the stance phase as well. In particular, unlike in running, the knee absorbs power during the portion of stance in which the ankle is generating power. As such, unlike in running, the knee cannot be characterized in the stance phase of walking as consisting of substantially an absorption and propulsion phase. Unlike in running, the knee and ankle do not act energetically in synchrony in the stance phase of walking. And unlike in running, the amount of power generated by the knee in walking is not greater than or essentially equal to the amount of power absorbed. Note that all these fundamental distinctions are aspects of the stance phase.

FIG. 31 shows the (body-mass-normalized) power characteristics of the knee and ankle joints during the stance phase of running for healthy subjects. As shown therein, FIG. 31 clearly shows that running stance phase consists of an absorption phase (negative net power in both joints) and a propulsion phase (positive net power in both joints). Further, FIG. 31 also clearly shows that the two joints are essentially operating in synchrony. FIG. 32 shows the (body-mass-normalized) power characteristics of the knee and ankle during the stance phase of walking for healthy subjects. In contrast to FIG. 31, FIG. 32 clearly shows the absence of the two phases, particularly for the knee joint, and clearly indicating the lack of energetic synchrony. Further, FIG. 31 also clearly shows that the knee generates net energy during the stance phase of running, while FIG. 32 clearly shows the knee dissipates net energy during the stance phase of walking. It should be noted that the swing phase of running and walking (not shown in the figures) are essentially the same, wherein the fundamental behavior of both entails the initial flexion and subsequent extension of the knee (although running is more exaggerated), and entails relatively little ankle movement.

Due to the fundamental behavioral distinctions during the stance phase between a bipedal walking and running gait, a controller for a powered prosthetic, orthotic, or assistive device that generates a running gait must be constructed in a fundamentally different manner from a controller that provides a walking gait. That is, a walking controller cannot produce a running gait, and vice-versa. In particular, assuming a running controller is implemented in a finite state construction, the stance phase of a running controller for a prosthesis that consists of at least a knee joint and possibly also an ankle joint must essentially consist of two finite states, one that provides the essential behavior of the absorption phase of stance and one that provides the essential behavior of the propulsion phase of stance. In the absorption phase, the knee and ankle (if included) joints should dissipate power, while in the propulsion phase, the knee and ankle (if included) should generate power, roughly equal to or greater than the amount dissipated. An exemplary method for power dissipation is by use of a passive impedance function. That is, configuring the joint to emulate a passive impedance such as a stiffness component, damping component, or both. By definition, a passive system, over time, does not generate net (positive) power. The passive impedance function can consist of the sum of a passive stiffness function and a passive damping function. Such a passive stiffness function should relate joint torque to angle in a single valued, odd algebraic function, while the passive damping function should relate joint torque to angle in an odd algebraic function. In this case, the passivity of the functions will guarantee that energy is absorbed if the joint is returned to an original at rest configuration. In the propulsion phase, the knee and ankle (if included) joints should generate power according to any of a number of possible methods.

In addition to differing states, a running controller must have differing switches to move between the respective states. In particular, a condition must exist in a running controller to move from the absorption phase to the propulsion phase of stance. In an exemplary method, this switching can be based on the angular velocity of the knee joint, and in particular, when the angular velocity of the knee joint reaches zero (i.e., the knee has stopped flexing in the absorption phase of stance). Alternatively, in another exemplary method, the knee and ankle joints can switch from the absorption to the propulsion phase when the load measured by the leg has reached a maximum. Note that neither of these conditions would work effectively in a walking controller, even if used strictly for the ankle, since the start of ankle push-off in walking does not correspond to either a joint angular velocity reversal or peak load measurement. An example of an exemplary running controller for a powered prosthesis with a knee and ankle joint is shown in FIG. 33.

Since an amputee cannot run with a walking controller, nor walk with a running controller, a running controller should be complemented with a method to detect a user's intent to switch between walking and running. In the various embodiments, the controller can switch from a walking controller to a running controller if the detected magnitude of load at heel strike is greater than a threshold load. Similarly, the controller can switch from the running controller back to a walking controller based on the length of time the user is in stance phase.

Other methods can also be used to infer intent to switch between walking and running modes. For example, the intent recognizer can infer intent to transition between the walking controller and the running controller based on a measurement of at least a load or acceleration at foot strike. However, the intent recognizer can also infer intent to transition between a walking controller and the running controller based on estimation of cadence, a measurement of at least stance time, swing time, or stride time, or a measurement of at least thigh motion. The thigh motion can be a measurement of thigh angular velocity.

II. Exemplary Running Controller Implementation

As noted above, a controller of a powered prosthesis can be structured in three levels. The lowest level controls torque at both the knee and ankle joints. The middle level controller generates a torque reference for the lowest level controller. The middle level controller is a finite-state machine, each state defined by passive impedance characteristics for both the knee and ankle. Specifically, the required (knee and ankle) joint torques in each state are characterized by a set of impedance parameters corresponding to the model set forth above in equation 1. Transitions between gait modes or states are triggered by certain biomechanical conditions being met. Further, a separate controller exists for each activity implemented in the prosthesis and at any given time during operation the appropriate middle level controller is selected by the highest level controller.

The various embodiments of the invention provide a finite-state (middle level) controller for running gait that can be integrated into the aforementioned high level controller. Gait modes were determined by an iterative least squares regression application of (1) to a set of running gait data, intended to specify the smallest number of (stable) gait modes which sufficiently modeled healthy running. This model has five distinct gait modes (one mode is divided into two submodes) and corresponding sets of parameters. Within this controller, running gait is divided into: landing/absorption (Mode 0), propulsion (Mode 1), swing flexion (Mode 2), and swing extension (mode 3), where the propulsion mode can consist of two submodes, push-off (Mode 1A) and toe-off (Mode 1B). These modes and their transition conditions are depicted by the running controller in FIG. 34, which is a specific implementation of the running controller in FIG. 33. However, it should be noted that the configuration in FIG. 34 is presented by way of example and not by way of limitation. That is, other implementations of the running controller of FIG. 33 may have more or less features than the configuration of FIG. 34.

As noted above, Modes 0 and 1 are stance modes for absorption and propulsion, respectively, which in healthy running biomechanics, should comprise less than 50% of a stride. Modes 2 and 3 are swing modes, which in healthy running biomechanics comprise greater than 50% of a stride. While in Mode 0, both the knee and ankle have a relatively high stiffness. The knee flexes in a controlled manner, providing shock absorption and bearing the user's weight. The ankle initially plantarflexes in order to reach a flat-foot state and then dorsiflexes as the user's body center passes over the foot. Once the knee reaches peak flexion for the stance phase and naturally begins to extend (inferred by a zero crossing in velocity), indicating a natural transition into a power generation phase, the controller transitions into Mode 1, the propulsion phase.

During Mode 1, the knee and ankle actively extend and plantarflex, respectively, in order to propel the user forward and upward. As noted above, Mode 1 can have two sub-modes: a Push-off mode (Mode 1A) and a Toe-off mode (Mode 1B). During Mode 1A, the knee and ankle actively extend and plantarflex. Mode 1A will then transition to Mode 1B as soon as the knee reaches peak stance knee extension (a zero crossing in knee velocity), indicating a natural transition into the swing mode characterized by knee flexion. During Mode 1B, the knee begins to flex as the ankle continues to plantarflex, which assists in flexion of the knee. Note that mode 1B is very brief and typically coincides with conditions facilitating near immediate transition into Mode 2.

Upon detecting that the foot is off the ground—for example, once sensors on the prosthesis indicate that the load on the prosthesis has fallen below a threshold—Mode 1 will transition to Mode 2. During Mode 2, the knee flexes, and the ankle returns to a slightly dorsiflexed state in order to prepare for the next heel strike. Mode 2 will then transition to Mode 3 as soon as the knee naturally begins to extend (a zero crossing in knee angular velocity), indicating a natural transition into knee extension. During Mode 3, the knee further extends, preparing for heel strike. Once the heel strike is detected, Mode 3 can transition back to Mode 0. For example, once sensors on the prosthesis indicate that the load on the prosthesis is above a load threshold similar to that employed in the transition from Mode 1 to Mode 2. Further, as shown in the state flow diagram in FIG. 33, if during any aerial mode (modes 2 and 3, i.e., where the foot is off the ground) a load is detected (i.e., foot strike detected), the controller immediately transitions to the landing or absorption mode (Mode 0).

As noted above, the running controller of FIG. 34 can be complemented with a method to detect a user's intent (e.g., within the intent recognizer discussed above) to switch between walking and running. For example, the intent recognizer can switch from the walking controller to the running controller if the detected magnitude of load at foot strike is greater than a threshold which is greater than the load seen during heel strike in walking, that is, detecting an attempt at a running stride by detecting the typical impact on a limb during running. Note that this threshold is not intended to distinguish whether the user is placing weight on the prosthesis, as in the running controller, but to distinguish a load typical of running from a load typical of walking. Similarly, the controller can switch from the running controller back to a walking controller based on the length of time the user is in stance phase or swing phase, or the duration of a stride. For example, if the user remains at Mode 0 and/or Mode 1 for an extended period of time or if the user has a significantly longer stride duration than the previous stride.

Other potential switching conditions between walking and running include 1) a threshold of estimated percent of stride (essentially based on stride time and estimated cadence) at the start (or end) of swing, 2) a threshold for peak thigh absolute angular velocity during swing, 3) a threshold for load at foot strike, 4) a threshold for shank acceleration at foot strike, and 5) some combination of the above.

III. Running Controller Evaluation

Based on the parameters derived from the aforementioned least squares regression, the controller's basic function was verified by a healthy subject fitted with an able-bodied adapter, immobilizing the user's knee at roughly 100° of knee flexion. Once this preliminary verification was complete, the prosthesis was fitted to a unilateral transfemoral amputee, and the impedance parameters were tuned to suit the gait biomechanics of the amputee subject.

A. Evaluation Metrics

The overarching goal of a running controller in accordance with the various embodiments is to enable or improve running gait in the user, specifically in situations when it is not feasible for the user to doff his or her daily use prosthesis and don a running prosthesis. Moreover, the performance objective of the running controller of the various embodiments is to reproduce, as faithfully as possible, the function provided by the intact limb that the prosthesis has replaced. Thus, the running controller can be evaluated based on its ability to provide sagittal plane joint angles representative of healthy running, the presence of a double float phase, and on the degree of consistency in stride-to-stride gait mode transitions.

In order to obtain reference data representative of healthy running, motion capture data was collected on a small set of healthy subjects. For the motion capture study, five healthy subjects-males ages 24-26—each ran on a treadmill at a speed of 2.25 $ms^{-1}$ for two trials, forty-five seconds each. The motion capture was achieved with twelve OptiTrack S250e high speed infrared cameras running at 120 Hz using ARENA motion capture software. Thirty-four reflective markers were placed on each subject corresponding to a full skeleton (similar to the Helen Hayes marker set); the software's skeleton solver was used to track the subject's motion. The data collected in ARENA was subsequently processed in MATLAB in order to extract lower limb sagittal joint angles. The joint angles were parsed into single strides (twenty strides per trial) and normalized to a time base of 100%. An offset was applied to the ankle for each subject based upon the angle of the foot with respect to the ground plane during a period where the subject's foot was known to be flat on the ground. The mean and standard deviation over all strides were calculated for each joint.

B. Experimental Tuning

The amputee subject who participated in the running controller evaluation was a 23-year-old male, 4 years post-amputation. The subject's amputation was the result of a traumatic injury; his daily use prosthesis is an Otto-Bock CLeg with a Freedom Innovations Renegade foot.

The middle level running controller impedance parameters were tuned experimentally on the treadmill during two sessions. The impedance parameters and mode transition thresholds employed during the initial controller verification with a healthy subject were used as a starting point for tuning with the amputee subject, with the spring constants in the stance modes reduced for user comfort. The impedance parameters were iteratively tuned based upon a combination of knee and ankle joint angles data, qualitative video analysis, and user feedback/comfort. The experimentally tuned impedance parameters are shown in Table 1.

TABLE I

| | IMPEDANCE PARAMETERS | | | | | |
| | Knee | | | Ankle | | |
| Gait Mode | k $\left(\dfrac{Nm}{deg}\right)$ | b $\left(\dfrac{Nms}{deg}\right)$ | $\theta_{eq}$ (deg) | k $\left(\dfrac{Nm}{deg}\right)$ | b $\left(\dfrac{Nms}{deg}\right)$ | $\theta_{eq}$ (deg) |
|---|---|---|---|---|---|---|
| 0 | 4.0 | 0.1 | 20.0 | 5.5 | 0.2 | 10.0 |
| 1 | 4.5 | 0.1 | 23.0 | 3.0 | 0.1 | −18.0 |
| 2 | 3.5 | 0.2 | 70.0 | 2.0 | 0.1 | −18.0 |
| 3 | 3.5 | 0.15 | 70.0 | 1.0 | 0.1 | 5.0 |
| 4 | 0.9 | 0.15 | 20.0 | 3.0 | 0.2 | 5.0 |

Following tuning, the controller was evaluated in trials in which the amputee subject ran on a treadmill at 2.25 ms$^{-1}$ (5.0 mph); the subject was allowed to utilize the treadmill's handrails. Note that, for the amputee subject wearing the powered prosthesis with running controller, this treadmill speed corresponded to a cadence of 130 steps per minute.

FIG. 35 depicts six key elements of a stride captured from a video taken during one trial. FIG. 36 depicts the mode transitions (percent of stride)±one standard deviation as recorded during the running controller evaluations. This figure demonstrates the consistency of gait mode transitions within the running controller. One should note that Mode 1B (toe-off) comprises, on average, less than 3% of stride; this mode was intended to serve as an overlap for Mode 1A in the ankle and Mode 2 in the knee, allowing the knee to flex while the ankle continues to plantarflex.

FIG. 37 compares sagittal plane knee joint angles (a) and ankle joint angles (b) for several consecutive strides of the amputee subject running on the powered prosthesis to the same angles for healthy subjects (obtained from the aforementioned healthy subject motion capture study of running, also at 2.25 ms$^{-1}$). One should first note that the standard deviation of the mean for healthy subjects reflects variety in the running gaits of healthy subjects. While the healthy subjects did exhibit overall uniformity concerning the features of the joint angle curves (except in the ankle near toe-off), range of motion varied considerably between subjects. Concerning the powered prosthesis, the salient features of the running gait, in both the knee and ankle angles, generally match those of the healthy subjects. That is, relative to walking, the knee and ankle joints both achieve a considerably greater degree of flexion and dorsiflexion, respectively, during the stance phase. The most noticeable deviation between the healthy subject data and the powered prosthesis data is the slight mismatch in knee joint kinematics in the mode transition from 0 to 1. This may indicate the need for an additional (brief) gait mode which might better transition between 0 and 1 or a slight adjustment in switching conditions.

As previously mentioned, another significant feature of running gait, in addition to another significant distinction between walking and running, is that the latter has a stance phase that last less than 50% of the stride, which generates a double float phase of gait (as opposed to the double support phase that characterizes walking). Specifically, the stance phase of running has been reported to last between 39% and 45% of the stride. Mode 3, which indicates toe-off in the powered prosthesis gait cycle (i.e., the termination of the stance phase), begins on average at approximately 45% of stride. As such, the powered prosthesis and running controller provides the relative duration of stance and swing phases that characterizes a running gait and distinguishes it from a walking gait. Visual evidence of the double float phase of gait, as provided by the powered prosthesis, is shown in FIG. 35.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method of using a device, providing the device comprising a plurality of powered joints of a lower limb device, in which the plurality of powered joints includes a powered knee joint including a first stiffness component, a first dampening component and a first motor for providing an output torque at the powered knee joint and a powered ankle joint including a second stiffness component, a second dampening component and a second motor for providing an output torque at the powered ankle joint and a non-transitory computer-readable medium having stored thereon a plurality of instructions for causing a controller device for the plurality of powered joints of the lower limb device to perform the method comprising:

configuring the lower limb device to a current state in a finite state model for an activity mode comprising a running mode;

collecting real-time sensor information for the lower limb device from real-time sensors;

based on real-time sensor information for the lower limb device, transitioning the lower limb device from the current state in the finite state model to a subsequent state in the finite state model for the current activity mode when a pre-defined criteria for transitioning to the subsequent state is met; and repeating the transitioning until the activity mode of the lower limb device changes from the running mode, wherein the finite state model comprises an absorption phase, a propulsion phase, a swing flexion phase, and a swing extension phase, wherein the absorption phase is configured to transition to the propulsion phase, wherein the propulsion phase is configured to transition to the swing flexion phase, wherein the swing flexion phase is configured to transition to the swing extension phase, and wherein the swing extension mode is configured to transition to the absorption phase, wherein transitioning into the absorption phase occurs when a load on the lower limb device increased above a first threshold;

and, wherein the powered knee and ankle joints are each configured in the absorption phase to behave as a combined stiffness and damping, the stiffness and damping components configured such that the powered knee and ankles joints absorb energy associated with decelerating a vertical motion of a body center of mass, wherein transitioning into the propulsion phase occurs when the powered knee joint has absorbed the load on the lower limb device, and wherein the first and second motors of the powered knee and ankle joints are each controlled configured in the propulsion phase such that the powered knee and ankles joints generate energy associated with accelerating the vertical motion of the body's center of mass.

2. The method of claim 1, wherein the non-transitory computer-readable medium further comprises instructions for causing at least one processor to:

Select the running mode for the lower limb device based on the real-time sensor information during a walking mode prior to operating the powered knee joint and the powered ankle joint, wherein a transition between the walking mode and the running mode is based on a measurement of at least one of a load or acceleration at foot strike, a stance time, a swing time, or a stride time.

3. The method of claim 1, wherein the propulsion phase further comprises a first sub-mode and a second sub-mode, wherein the first sub-mode comprises active extension and plantarflexion of both the powered knee joint and the powered ankle joint, and wherein the second sub-mode comprises flexing of the powered knee joint while the powered ankle joint continues to plantarflex to assist the flexing of the powered knee joint.

4. The method of claim 1, wherein the swing flexion phase comprises:

transitioning into the swing flexion phase by detecting a load on the lower limb device decreased below a second threshold;

flexing the powered knee joint; and configuring the powered ankle joint to a dorsiflexed state.

5. The method of 1, wherein the swing extension phase comprises: transitioning into the swing extension phase by detecting that a velocity of the powered knee joint is at a threshold velocity for extension; further extending the powered knee joint;

detecting that a load on the lower limb device increased above the first threshold;

and completing the swing extension mode.

6. A system for controlling a lower limb device comprising a plurality of powered joints, the plurality of powered joints including a powered knee joint and a powered ankle joint, the powered knee joint including a first motor for providing an output torque at the powered knee joint, the powered ankle joint including a second motor for providing an output torque at the powered ankle joint, the system comprising:

at least one sensor for collecting real-time sensor information for the lower limb device;

at least one processor communicatively coupled to the at least one sensor and to the powered knee joint; and a computer-readable medium, having stored thereon instructions for causing the at least one processor to perform the steps of:

generating control signals for the powered knee joint to transition the lower limb device to a current state in a finite state model for an activity mode comprising a running mode;

generating additional control signals for the powered knee joint to transition the lower limb device from the current state to a subsequent state in the finite state model for the current activity mode when a pre-defined criteria for transitioning to the subsequent state is met based on the real-time sensor information; and repeating the generating of the additional control signals for transitioning until the activity mode changes of the lower limb device changes from the running mode, wherein the finite state model comprises an absorption phase, a propulsion phase, a swing flexion phase, and a swing extension phase, wherein the absorption phase is configured to transition to the propulsion phase, wherein the propulsion phase is configured to transition to the swing flexion phase, wherein the swing flexion phase is configured to transition to the swing extension phase, and wherein the swing extension mode is configured to transition to the absorption phase, wherein transitioning into the absorption phase occurs when a load on the lower limb device increased above a first threshold, and, wherein the powered knee and ankle joints are each configured in the absorption phase to behave as a combined stiffness and damping, the stiffness and damping components configured such that the powered knee and ankles joints absorb energy associated with decelerating a vertical motion of a body center of mass, wherein transitioning into the propulsion phase occurs when the powered knee joint has absorbed the load on the lower limb device, and wherein the powered knee and ankle joints are each configured in the propulsion phase such that the powered knee and ankles joints generate energy associated with accelerating the vertical motion of the body center of mass.

7. The system of claim 6, wherein the computer-readable medium further comprises instructions for causing the at least one processor to:

selecting the running mode for the lower limb device based on the real-time sensor information during a walking mode prior to operating the powered knee joint and the powered ankle joint, wherein a transition between the walking mode and the running mode is based on a measurement of at least one of a load or acceleration at foot strike, a stance time, a swing time, or a stride time.

8. The system of claim 6, wherein the propulsion phase further comprises a first sub-mode and a second sub-mode, wherein the first sub-mode comprises active extension and plantarflexion of both the powered knee joint and the powered ankle joint, and wherein the second sub-mode comprises flexing of the powered knee joint while the powered ankle joint continues to plantarflex to assist the flexing of the powered knee joint.

9. The system of claim 6, wherein the swing flexion phase comprises:

transitioning into the swing flexion phase by detecting a load on the lower limb device decreased below a second threshold;

flexing the powered knee joint; and configuring the powered ankle joint to a dorsiflexed state.

10. The system of claim 6, wherein the swing extension phase comprises:

transitioning into the swing extension phase by detecting that a velocity of the powered knee joint is at a threshold velocity for extension;

further extending the powered knee joint;

detecting that a load on the lower limb device increased above the first threshold; and completing the swing extension mode.

\* \* \* \* \*